(12) United States Patent
Huttemann

(10) Patent No.: US 7,473,530 B2
(45) Date of Patent: Jan. 6, 2009

(54) METHOD TO DETECT LUNG CANCER

(75) Inventor: Maik Huttemann, Grosse Pointe, MI (US)

(73) Assignee: Wayne State University, Detriot, MI (US)

(*) Notice: Subject to any disclaimer, the term of this patent is extended or adjusted under 35 U.S.C. 154(b) by 0 days.

(21) Appl. No.: 11/381,653

(22) Filed: May 4, 2006

(65) Prior Publication Data

US 2006/0257898 A1 Nov. 16, 2006

Related U.S. Application Data

(60) Provisional application No. 60/677,776, filed on May 4, 2005.

(51) Int. Cl.
*C12Q 1/68* (2006.01)
(52) U.S. Cl. ...................................................... 435/6
(58) Field of Classification Search ................ None
See application file for complete search history.

(56) References Cited

OTHER PUBLICATIONS

Tockman et al (Cancer Res., 1992, 52:2711s-2718s).*
"Cancer facts and figures 2002", http://www.cancer.org/downloads/STT/CancerFacts&Figures2002TM.pdf, American Cancer Society,(2002),1-48.
Acin-Perez, R. , et al., "An intragenic suppressor in the cytochrome c oxidase I gene of mouse mitochondrial DNA", *Hum Mol Genet.*, 12(3), (2003),329-39.
Archer, S. , et al., "The mechanism(s) of hypoxic pulmonary vasoconstriction: potassium channels, redox O(2) sensors, and controversies.", *News Physiol Sci.*, 17, (2002),131-7.
Arnold, S. , et al., "3,5-Diiodothyronine binds to subunit Va of cytochrome-c oxidase and abolishes the allosteric inhibition of respiration by ATP", *Eur J Biochem.*, 252(2), (1998),325-30.
Arnold, S. , et al., "Cell respiration is controlled by ATP, an allosteric inhibitor of cytochrome-c oxidase", *Eur J Biochem.*, 249(1), (1997),350-4.
Arnold, S , et al., "The intramitochondrial ATP/ADP-ratio controls cytochrome c oxidase activity allosterically", *FEBS Lett.*, 443(2), (1999),105-8.
Avanzo, J. L., et al., "Increased susceptibility to urethane-induced lung tumors in mice with decreased expression of connexin43.", *Carcinogenesis*, 25(10), (2004),1973-82.
Barros, R. C., et al., "Hypoxic metabolic response of the golden-mantled ground squirrel", *J Appl Physiol.*, 91(2), (2001),603-12.
Baty, J. W., et al., "Detection of oxidant sensitive thiol proteins by fluorescence labeling and two-dimensional electrophoresis", *Proteomics*, 2(9), (2002),1261-6.
Bender, E. , et al., "The allosteric ATP-inhibition of cytochrome c oxidase activity is reversibly switched on by cAMP-dependent phosphorylation.", *FEBS Lett.*, 466(1), (2000), 130-4.
Boehle, A. S., et al., "Wortmannin inhibits growth of human non-small-cell lung cancer in vitro and in vivo", *Langenbecks Arch Surg.*, 387(5-6), (2002),234-9.

Boerner, J. L., et al., "Phosphorylation of Y845 on the epidermal growth factor receptor mediates binding to the mitochondrial protein cytochrome c oxidase subunit II.", *Mol Cell Biol.*, 24(16), (2004), 7059-71.
Brand, M. D., et al., "Stimulation of the electron transport chain in mitochondria isolated from rats treated with mannoheptulose or glucagon", *Arch Biochem Biophys.*, 283(2), (1990),278-84.
Burgess, J, W., et al., "cAMP-dependent protein kinase isozymes with preference for histone H2B as substrate in mitochondria of bovine heart.", *Biochem Cell Biol.*, 65(2), (1987), 137-43.
Burke, P. V., et al., "Structure/function of oxygen-regulated isoforms in cytochrome c oxidase", *J Exp Biol.*, 201 (Pt 8), (1998), 1163-75.
Cantley, L. C., "The phosphoinositide 3-kinase pathway.", *Science*, 296(5573), (2002), 1655-7.
Cardone, L. , et al., "Mitochondrial AKAP121 binds and targets protein tyrosine phosphatase D1, a novel positive regulator of src signaling.", *Mol Cell Biol.*, 24(11), (2004),4613-26.
Chandel, N. S., et al., "Cellular oxygen sensing by mitochondria: old questions, new insight.", *J Appl Physiol.*, 88(5), (2000), 1880-9.
Chandel, N. S., et al., "Mitochondrial reactive oxygen species trigger hypoxia-induced transcription", *Proc Natl Acad Sci U S A.*, 95(20), (1998), 11715-20.
Chen, R. , et al., "The phosphorylation of subunits of complex I from bovine heart mitochondria", *J Biol Chem.*, 279(25), (2004),26036-45.
Corso, M. , et al., "Protein phosphorylation in mitochondria from human placenta", *Placenta*, 22(5), (2001),432-9.
Cuezva, J. M., et al., "Mitochondrial biogenesis in the liver during development and oncogenesis.", *J Bioenerg Biomembr.*, 29(4), (1997), 365-77.
Cumsky, M. G., et al., "Structural analysis of two genes encoding divergent forms of yeast cytochrome c oxidase subunit V.", *Mol Cell Biol.*, 7(10), (1987), 3511-9.
Dal Piaz, V. , et al., "Phosphodiesterase 4 inhibitors, structurally unrelated to rolipram, as promising agents for the treatment of asthma and other pathologies.", *Eur J Med Chem.*, 35(5), (2000),463-80.
Dignam, J. D., et al., "Accurate transcription initiation by RNA polymerase II in a soluble extract from isolated mammalian nuclei.", *Nucleic Acids Res.*, 11(5), (1983), 1475-89.
Dimino, M. J., et al., "Cyclic AMP-dependent protein kinase in mitochondria and cytosol from different-sized follicles and corpora lutea of porcine ovaries.", *J Biol Chem.*, 256(21), (1981), 10876-82.
Eng, J. K., et al., "An approach to correlate tandem mass spectral data of peptides with amino acid sequence in a protein database", *Journal of the American Society for Mass Spectrometry*, 5, (1994),976-989.
Epstein, M. A., et al., "A theoretical analysis of the barometric method for measurement of tidal volume", *Respir Physiol.*, 32(1), (1978),105-20.

(Continued)

*Primary Examiner*—Misook Yu
*Assistant Examiner*—Sean Aeder
(74) *Attorney, Agent, or Firm*—Schwegman, Lundberg & Woessner, P.A.

(57) ABSTRACT

Certain embodiments of the present invention relate to methods for detecting lung cancer.

21 Claims, 3 Drawing Sheets

OTHER PUBLICATIONS

Esamai, F. O., et al., "Relationship between exposure to tobacco smoke and bronchial asthma in children: a review", *East Afr Med J.*, 75(1), (1998),47-50.

Ferguson-Miller, S., et al., "Correlation of the kinetics of electron transfer activity of various eukaryotic cytochromes c with binding to mitochondrial cytochrome c oxidase.", *J Biol Chem.*, 251(4), (1976),1104-15.

Ferguson-Miller, S., et al., "Definition of cytochrome c binding domains by chemical modification. III. Kinetics of reaction of carboxydinitrophenyl cytochromes c with cytochrome c oxidase", *J Biol Chem.*, 253(1), (1978),149-59.

Frank, V., et al., "Regulation of the H+/e- stoichiometry of cytochrome c oxidase from bovine heart intramitochondrial ATP/ADP ratios.", *FEBS Lett.*, 382(1-2), (1996),121-4.

Frohrnan, M. A., *PCR Primer, A Laboatorial Manual*, Dieffenbach, C. W., and Dveksler, G. S., Eds., Cold Spring Harbor Laboratory Press, Cold Spring Harbor, NY,(1995),381-409.

Garber, E. A., et al., "Interaction of cytochrome c with cytochrome c oxidase: an understanding of the high- to low-affinity transition.", *Biochim Biophys Acta.*, 1015(2), (1990),279-87.

Gnaiger, E., et al., "Mitochondrial oxygen affinity, respiratory flux control and excess capacity of cytochrome c oxidase ", *J Exp Biol.*, 201(Pt 8), (1998), 1129-39.

Green, R. H., et al., "Management of asthma in adults: current therapy and future directions", *Postgrad Med J.*, 79(931), (2003), 259-67.

Griffioen, G., et al., "Molecular mechanisms controlling the localisation of protein kinase A.", *Curr Genet.*, 41(4), (2002),199-207.

Grossman, L. I., et al., "Nuclear genes for cytochrome c oxidase.", *Biochim Biophys Acta.*, 1352(2), (1997), 174-92.

Gyuris, J., et al., "Cdi1, a human G1 and S phase protein phosphatase that associates with Cdk2", *Cell*, 75(4), (1993),791-803.

Heinemeyer, T., et al., "Databases on transcriptional regulation: TRANSFAC, TRRD and COMPEL.", *Nucleic Acids Res.*, 26(1), (1998),362-7.

Hirsch, F. R., et al., "Prevention and early detection of lung cancer-clinical aspects.", *Lung Cancer*, 17(1), (1997),163-74.

Huttemann, M., et al., "A third isoform of cytochrome c oxidase subunit VIII is present in mammals", *Gene*, 312, (2003),95-102.

Huttemann, M., et al., "Cytochrome c oxidase of mammals contains a testes-specific isoform of subunit VIb—the counterpart to testes-specific cytochrome c?", *Mol Reprod Dev.*, 66(1), (2003),8-16.

Huttemann, M., et al., "Mammalian subunit IV isoforms of cytochrome c oxidase", *Gene*, 267(1), (2001),111-23.

Huttemann, M., "Partial heat denaturation step during reverse transcription and PCR screening yields full-length 5'-cDNAs", *Biotechniques*, 32(4), (2002),730, 732, 734, 736.

Jaakkola, Panu , "Targeting of HIF-alpha to the von Hippel-Lindau Ubiquitylation Complex by O2-Regulated Prolyl Hydroxylation", *Science*, 292(5516), (2001),468-472.

Jackson, S. P., et al., "GC box binding induces phosphorylation of Sp1 by a DNA-dependent protein kinase", *Cell*, 63(1), (1990),155-65.

Jacky, J. P., "Barometric measurement of tidal volume: effects of pattern and nasal temperature", *J Appl Physiol.*, 49(2), (1980), 319-25.

Jiang, F., et al., "Absence of cardiolipin in the crd1 null mutant results in decreased mitochondrial membrane potential and reduced mitochondrial function.", *J Biol Chem.*, 275(29), (2000),22387-94.

Joad, J. P., et al., "Passive smoke effects on cough and airways in young guinea pigs: role of brainstem substance P", *Am J Respir Crit Care Med.*, 169(4), (2004),499-504.

Kadenbach, B., et al., "Isozymes of cytochrome-c oxidase: characterization and isolation from different tissues", *Methods Enzymol.*, 126, (1986),32-45.

Kadenbach, B., et al., "Regulation of mitochondrial energy generation in health and disease", *Biochim Biophys Acta*, 1271, (1995),103-9.

Kadenbach, B., et al., "Separation of mammalian cytochrome c oxidase into 13 polypeptides by a sodium dodecyl sulfate-gel electrophoretic procedure", *Anal Biochem.*, 129, (1983),517-21.

Kadenbach, Bernhard, et al., "The possible role of cytochrome c oxidase in stress-induced apoptosis and degenerative diseases", *Biochimica et Biophysics Acta 1655*, (2004),400-408.

King, M. P., et al., "Human cells lacking mtDNA: repopulation with exogenous mitochondria by complementation", *Science*, 246(4929), (1989),500-3.

Kleitke, B., et al., "Evidence for cyclic AMP-dependent protein kinase activity in isolated guinea pig and rat liver mitochondria.", *Acta Biol Med Ger.*, 35(3-4), (1976),K9-K17.

Kolonin, M. G., et al., "Interaction mating methods in two-hybrid systems", *Methods Enzymol.*, 328, (2000),26-46.

Kondrashin, A. A., et al., "Subcellular distribution of the R-subunits of cAMP-dependent protein kinase in LS-174T human colon carcinoma cells.", *Biochem Mol Biol Int.*, 45(2), (1998), 237-44.

Korshunov, S. S., et al., "High protonic potential actuates a mechanism of production of reactive oxygen species in mitichondria.", *FEBS Lett.*, 416(1), (1997),15-8.

Kosower, N. S., et al., "Diamide: an oxidant probe for thiols", *Methods Enzymol.*, 251, (1995), 123-33.

Lando, D., et al., "Asparagine hydroxylation of the HIF transactivation domain a hypoxic switch", *Science*, 295(5556), (2002),858-61.

Lee, I., et al., "Control of mitochondrial membrane potential and ROS formation by reversible phosphorylation of cytochrome c oxidase", *Mol Cell Biochem.*, 234-235(1-2), (2002),63-70.

Lee, I., et al., "New control of mitochondrial membrane potential and ROS formation—a hypothesis", *Biol Chem.*, 382(12), (2001),1629-36.

Lee, I., et al., "Palmitate decreases proton pumping of liver-type cytochrome c oxidase", *Eur J Biochem.*, 268(24), (2001),6329-34.

Li, J., et al., " Lung pathology in platelet-derived growth factor transgenic mice: effects of genetic background and fibrogenic agents.", *Exp Lung Res.*, 28(6), (2002), 507-22.

Licklider, L. J., et al., "Automation of Nanoscale Microcapillary Liquid Chromatography-Tandem Mass Spectrometry with a Vented Column", *Analytical Chemistry*, 74(13), (2002),3076-3083.

Lin, X., et al., "Overexpression of phosphatidylinositol 3-kinase in human lung cancer", *Langenbecks Arch Surg.*, 386(4). (2001),293-301.

Lundblad, L. K., et al., "A reevaluation of the validity of unrestrained plethysmography in mice", *J Appl Physiol.*, 93(4), (2002), 1198-207.

Malkinson, A. M., "The genetic basis of susceptibility to lung tumors in mice", *Toxicology*, 54(3), (1989),241-71.

Manning, G., et al., "The Protein Kinase Complement of the Human Genome", *Science*, 298(5600), (2002),1912-1934.

Michelakis, E. D., et al., "Diversity in mitochondrial function explains differences in vascular oxygen sensing", *Circ Res.*, 90(12), (2002),1307-15.

Miller, Y. E., et al., "Induction of a high incidence of lung tumors in C57BL/6 mice with multiple ethyl carbamate injections.", *Cancer Lett.*, 198(2), (2003), 139-44.

Miyazaki, T., et al., "Regulation of cytochrome c oxidase activity by c-Src in osteoclasts", *J Cell Biol.*, 160(5), (2003),709-18.

Muller, G., et al., "Protein phosphorylation in yeast mitochondria: cAMP-dependence, submitochondrial localization and substrates of mitochondrial protein kinases.", *Yeast*, 3(3), (1987),161-74.

Napiwotzki, J., et al., "ATP and ADP bind to cytochrome c oxidase and regulate its activity", *Biol Chem.*, 378(9), (1997),1013-21.

Ng, P. S., et al., "Protein-DNA footprinting by encapped duplex oligodeoxyribonucleotides", *Nucleic Acids Res.*, 32(13), (2004),e107.

Nilsson, M., et al., "Real-time monitoring of rolling-circle amplification using a modified molecular beacon design", *Nucleic Acids Res.*, 30(14), (2002),e66.

Ortega-Saenz, P., et al., "Rotenone selectively occludes sensitivity to hypoxia in rat carotid body glomus cells", *J Physiol.*, 548(Pt 3), (2003),789-800.

Osheroff, N., et al., "The reaction of primate cytochromes c with cytochrome c oxidase. Analysis of the polarographic assay.", *J Biol Chem.*, 258(9), (1983),5731-8.

Paddenberg, R., et al., "Essential role of complex II of the respiratory chain in hypoxia-induced ROS generation in the pulmonary vasculature.", *Am J Physiol Lung Cell Mol Physiol.*, 284(5), (2003),L710-9.

Papa, S., et al. "cAMP-dependent protein kinase and phosphoproteins in mammalian mitochondria. An extension of the cAMP-mediated intracellular signal transduction", *FEBS Lett.*, 444(2-3), (1999),245-9.

Pariset, C., et al., "Differential localization of two isoforms of the regulatory subunit RII alpha of cAMP-dependent protein kinase in human sperm: biochemical and cytochemical study", *Mol Reprod Dev.*, 39(4), (1994),415-22.

Pedersen, P. L., "Tumor mitochondria and the bioenergetics of cancer cells", *Prog Exp Tumor Res.*, 22, (1978),190-274.

Pohl, S. L., et al., "The glucagon-sensitive adenyl cyclase system in plasma membranes of rat liver. I. Properties", *J Biol Chem.*, 246(6), (1971),1849-56.

Robb-Gaspers, L. D., et al., "Integrating cytosolic calcium signals into mitochondrial metabolic responses", *EMBO J.*, 17(17), (1998),4987-5000.

Robinson-White, A., et al., "Protein kinase A signaling: "cross-talk" with other pathways in endocrine cells", *Ann N Y Acad Sci.*, 968, (2002),256-70.

Rodriguez-Enriquez, S., et al., "Intermediary metabolism of fast-growth tumor cells", *Arch Med Res.*, 29(1), (1998),1-12.

Rutter, J., et al., "Regulation of clock and NPAS2 DNA binding by the redox state of NAD cofactors", *Science*, 293(5529), (2001),510-4.

Ryan, J., et al., "KRAS2 as a genetic marker for lung tumor susceptibility in inbred mice", *J Natl Cancer Inst.*, 79(6), (1987),1351-7.

Santillan, A. A., et al., "A meta-analysis of asthma and risk of lung cancer (United States).", *Cancer Causes Control*, 14(4), (2003),327-34.

Schroedl, C., et al., "Hypoxic but not anoxic stabilization of HIF-1alpha requires mitochondrial reactive oxygen species", *Am J Physiol Lung Cell Mol Physiol.*, 283(5), (2002),L922-31.

Schuller, H. M., et al., "Neuroendocrine lung carcinogenesis in hamsters is inhibited by green tea or theophylline while the development of adenocarcinomas is promoted: implications for chemoprevention in smokers", *Lung Cancer*, 45(1), (2004),11-8.

Semenza, G. L., "HIF-1 and human disease: one highly involved factor", *Genes Dev.*, 14(16), (2000),1983-91.

Shoelson, S. E., et al., "Tryptic activation of insulin receptor. Proteolytic truncation of the alpha-subunit releases the beta-subunit from inhibitory control.", *J Biol Chem.*, 263(10), (1998),4852-60.

Siddiq, F., et al., "Increased osteonectin expression is associated with malignant transformation and tumor associated fibrosis in the lung.", *Lung Cancer*, 45(2), (2004),197-205.

Sodhi, C. P., et al., "Hypoxia and high glucose cause exaggerated mesangial cell growth and collagen synthesis: role of osteopontin.", *Am J Physiol Renal Physiol.*, 280(4), (2001), F667-74.

Speck, S. H., et al., "Single catalytic site model for the oxidation of ferrocytochrome c by mitochondrial cytochrome c oxidase.", *Proc Natl Acad Sci U S A.*, 81(2), (1984),347-51.

Steenaart, N. A., et al., "Mitochondrial cytochrome c oxidase subunit IV is phosphorylated by an endogenous kinase", *FEBS Lett.*, 415(3), (1997),294-8.

Suarez, M. D., et al., "The functional and physical form of mammalian cytochrome c oxidase determined by gel filtration, radiation inactivation, and sedimentation equilibrium analysis.", *J Biol Chem.*, 259(22), (1984), 13791-9.

Suh, Y. A., et al., "Cell transformation by the superoxide-generating oxidase Mox1", *Nature*, 401(6748), (1999),79-82.

Technikova-Dobrova, Z., et al., "Cyclic adenosine monophosphate-dependent phosphorylation of mammalian mitochondrial proteins: enzyme and substrate characterization and functional role", *Biochemistry*, 40(46), (2001), 13941-7.

Tsukihara, T., et al., "The low-spin heme of cytochrome c oxidase as the driving element of the proton-pumping process", *Proc Natl Acad Sci U S A.*, 100(26), (2003),15304-9.

Tsukihara, T., et al., "The whole structure of the 13-subunit oxidized cytochrome c oxidase at 2.8 A", *Science*, 272(5265), (1996), 1136-44.

Vaupel, P., et al. "Blood flow, oxygen and nutrient supply, and metabolic microenvironment of human tumors: a review.", *Cancer Res.*, 49(23), (1989),6449-65.

Villani, G., et al., "Low reserve of cytochrome c oxidase capacity in vivo in the respiratory chain of a variety of human cell types.", *J Biol Chem.*, 273(48), (1998),31829-36.

Von Wagenheim, K. H., et al., "Control of cell proliferation by progress in differentiation: clues to mechanisms of aging, cancer causation and therapy.", *J Theor Biol.*, 193(4), (1998),663-78.

Ward, J. P., "Mitochondria and oxygen sensing: fueling the controversy", *J Physiol.*, 548(Pt 3), (2003), 664.

Waypa, G. B., et al., "Mitochondrial reactive oxygen species trigger calcium increases during hypoxia in pulmonary arterial myocytes.", *Circ Res.*, 91(8), (2002),719-26.

Waypa, G. B., et al., "Model for hypoxic pulmonary vasoconstriction involving mitochondrial oxygen sensing", *Circ Res.*, 88(12), (2001),1259-66.

Wong-Riley, M., "Changes in the visual system of monocularly sutured or enucleated cats demonstrable with cytochrome oxidase histochemistry.", *Brain Res.*, 171(1), (1979),11-28.

Yamamoto, K., et al., "Fluorometric studies on the light chains of skeletal muscle myosin. I. Effects of temperature, ionic strength, divalent metal ions, and nucleotides.", *J Biochem* (Tokyo), 82(3), (1977),747-52.

You, M., et al., "Parental bias of Ki-ras oncogenes detected in lung tumors from mouse hybrids", *Proc Natl Acad Sci U S A.*, 89(13), (1992),5804-8.

Yu, M., et al., "Genomic organization and promoter regulation of human cytochrome c oxidase subunit VII heart/muscle isoform (COX7AH).", *Biochim Biophys Acta.*, 1574(3), (2002),345-53.

Yu, A. Y., et al., "Temporal, spatial, and oxygen-regulated expression of hypoxia-inducible factor-1 in the lung", *Am J Physiol.*, 275(4 Pt 1), (1998),L818-26.

Zhang, Q., et al., "Regulation of corepressor function by nuclear NADH", *Science*, 295(5561), (2002),1895-7.

Zhao, Y., et al., "Effect of cytochrome c on the generation and elimination of O2- and H2O2 in mitochondria", *J Biol Chem.*, 278(4), (2003),2356-60.

Zhong, J., et al., "A strategy for constructing large protein interaction maps using the yeast two-hybrid system: regulated expression arrays and two-phase mating", *Genome Res.*, 13(12), (2003),2691-9.

\* cited by examiner

SEQUENCE LISTING

```
<160> NUMBER OF SEQ ID NOS: 15

<210> SEQ ID NO 1
<211> LENGTH: 29
<212> TYPE: DNA
<213> ORGANISM: Homo sapiens

<400> SEQUENCE: 1
tacgagctca tgaaagtgtt gtgaagagc                                              29

<210> SEQ ID NO 2
<211> LENGTH: 19
<212> TYPE: DNA
<213> ORGANISM: Homo sapiens

<400> SEQUENCE: 2
gaagactttt cgctcccag                                                         19

<210> SEQ ID NO 3
<211> LENGTH: 29
<212> TYPE: DNA
<213> ORGANISM: Homo sapiens

<400> SEQUENCE: 3
ttggtggcag cgggtctacg tatttcctc                                              29

<210> SEQ ID NO 4
<211> LENGTH: 18
<212> TYPE: DNA
<213> ORGANISM: Homo sapiens

<400> SEQUENCE: 4
caaagccgat caccttga                                                          18

<210> SEQ ID NO 5
<211> LENGTH: 8576
<212> TYPE: DNA
```

<213> ORGANISM: Homo sapiens

<400> SEQUENCE: 5

| | | | | | |
|---|---|---|---|---|---|
| gagctccggg | gtgcccgagt | accgacagcc | aaagaagcat | ttacactttg | ccagataagg | 60 |
| aatcggctct | gcgaaggtgc | gaagaaccaa | atcctagcga | ttaatgtccc | aacaacgtga | 120 |
| acacttcctg | caactcgaaa | tcctcaaggg | aaactctgtc | gaatccccac | caagtgaacg | 180 |
| atgacttgtt | tctacaaagg | ctactgattt | caggaaacta | acgtataact | cgtcgcctta | 240 |
| aagtgcctct | aaaagcatcc | acgacggtta | aaagtcgctg | ctactacggg | acgctattta | 300 |
| ttcagcgcca | agacccaagc | gccatcgtgg | atcaccccat | tcctggccac | ggcaacccta | 360 |
| gggagcgggt | cctaggagcc | tgctggaggg | cgaccgctgg | gccagcttcc | tctctgctga | 420 |
| ctgaggggag | gccaggctgc | ctgcaagggg | aaggggccct | ttccgcgctt | accagggtga | 480 |
| gagccacctc | cagcatgggg | gcgagggcca | gggtgccgtg | aagaggggg | atgcagtcca | 540 |
| cgaagagggt | gtggtgggcg | ccggggccgc | ccagggggag | gtgctcctta | cgcggcttct | 600 |
| gcttctcggc | caccaggagc | ccgttgacgg | cgcagtgcgg | gtacttggcg | ccgtgcagca | 660 |
| ccatcttgca | gtaggcctgg | gtggtcagtt | tcaccccggg | catgctgacc | cgggagggcc | 720 |
| ccggaggccc | ctgggcgcgc | ggctgaggcc | tggacccgct | gcctggccgc | gcggcgcctc | 780 |
| agccgagaag | cgggacgagg | cggcggcgat | tgatggcgcg | gccgcgggct | ggcggggac | 840 |
| ccttcaggcc | cggccccgtt | tgggcctcgg | ctcctggaaa | agcgactcgc | gcctctggga | 900 |
| agccgcagcc | ccagactcca | gtcgcgcttc | tcgcccggcg | ccgccggaaa | gcagcctctc | 960 |
| caacgcctgc | cggaaagcag | cccggcccgg | cattttacga | cgttcgcagc | gctacccttt | 1020 |
| tccgctccac | ggtgacctcc | gtgcggccgg | gtgcgggcgg | agtcttcctc | gatcccgtgg | 1080 |
| tgctccgcgg | cgcggccttg | ctctcttccg | gtcgcgggac | accgggtgta | gagggcggtc | 1140 |
| gcggcgggca | gtggcggcag | gtgagacagg | aggtggccgg | tgcggcgccg | ccaggccggg | 1200 |
| ccgggtcggg | gggccgggag | ccatcaagtc | tgcacgtccg | cagcctggcc | gctcggcttc | 1260 |
| agcaggaagc | accgaatggg | cctcggagcc | aggtgacatt | gaggccggcc | cgtgggact | 1320 |
| ccgggctcgg | tggctccagg | ctcgggggc | cgccccgaag | tgcccggtcc | atcttacccg | 1380 |
| gtctcgcagc | ggctgcggac | cggcctcggg | cactgacctt | ggagcgcccg | ctggccgagg | 1440 |
| gctcaggctg | cggggaggcg | ggcccgcgct | ctgtgcctgc | agcctccgcc | cttgctcctt | 1500 |
| caaaaggtcc | ctgtgcaacc | cctcccgggt | tttgcgggac | tcccgggcgg | cgctcggctt | 1560 |
| tccagcctgg | aaggcgccta | ttgtttgctc | acgcaagggc | taggcccaag | gagagaagct | 1620 |
| agacgcgggc | gttcagccct | gacgtcatgc | ttgtttattc | tgccccaagg | agggtatttc | 1680 |
| cccacatcac | tctcaccagt | cctccgaagg | gtcgatttaa | agggggccgt | gtaaggttga | 1740 |
| tgggcctgaa | tagaggaggg | cccgggtgag | gggggtctc | ataggttttc | cgctctcctc | 1800 |
| agggattgga | aattgatcgg | ggctgtgttg | gcagccttct | ccaatttccc | cttctagtct | 1860 |
| atgtacaggc | ggtattaggt | tttaaaacac | tcagttgaat | gtgatgcgtg | ccacggtccc | 1920 |
| tgtgagctgt | cacctccccc | caccgctccc | tgaagaatgg | agcctgtcac | ggcagcacag | 1980 |
| tgctttaatg | atctctagct | ttttcagagt | caccttgtta | gcattttttc | ttcttgcctt | 2040 |
| tttttgtttg | agacggactc | ttgctctggt | tgcccaggct | ggggtgcagt | ggtgcggtct | 2100 |
| cggctcactg | cagtctctac | ctcccgggtt | caagcgattc | ttctacctca | gcctcccaag | 2160 |
| tagcggggat | tacggcgcc | cactaccatg | cccggctaat | ttttgtattg | ttagtagaga | 2220 |
| cgggatttca | ccatgttggc | caggctggtc | ttgaacccct | gacctcaggt | gatctgtccg | 2280 |

```
cctcggcctc ccaaagtgct ggaattaccg gcgtgagcca ccgcgcccgg cctctccttg    2340 ttttttttaaa aagaccaatg ttctgttaat tacctgaagc gcgtatatat tatggcagtt    2400
gatttataat gaagctcctt aaaagcatgc caattactaa gaaaaacctc atcctaggtc    2460
attttgtgaa ttcagagaca gtgataaaga atggatcatt tgcgttgggg agaagcaaac    2520
aaaaaaattc caaatgctc tggggcaaaa agaagactaa ttccttgctg tttgtcctta    2580
ttcatagaga aggtgtacat ttttatcttt cagaatgttg gctaccaggg tatttagcct    2640
agttggcaag cgagcaattt ccacctctgt gtgtgtacga gctcatggta agtgtgactt    2700
ttcttacttt taaataggct gaactaattt cattttgctc ctgctgtgta taaagccctg    2760
tgctggagtt ttaaagacct taattcggct cttgagggtc tttaggggag atataaatgt    2820
tctcacaggg cttggttcta gattaagaag tgtttataag tcaaattgaa tctcttctgg    2880
atctttggtt atactgatac ttccccactt acccttccct tccgttccac ttttttaagc    2940
ttcgaggatc taccccttc aaaaagatct tctgcaccat aactgactga ccttaatgac    3000
ctccctcccc accttgcccc cacaactccc aaccatttgc atcacctctg tttacattat    3060
agaggcaatg gaaacgaaag agcctggact tcctagcctg agctgggttt tcatctcatt    3120
tctatcaagg actagctact gaagctcagg aatctctttg ctcacctgaa gtatatggac    3180
agagcttagt tctgtgtctg gcatacagca catttacttt tgcatgtatc tggcgtctat    3240
ctactttgta ccagacactg ttaggcaccg agaagaaaaa gaatatgaaa tacacacact    3300
ttccaggagg ctgtttgcaa tctgaagagg gacggatggg tgaagacagt gttttattaa    3360
gagatggctc ctgggtagaa gcatttagcc cgatgtgggt ttcagggaag gcttctggag    3420
gaaactctcc agggtctttt cattgcctta gtagagtcta caccctgcct ggttagagct    3480
ggtcttgcct gcctttccga tcttattact gactgttgta ctcaaaaccc aaaaactacc    3540
atcagaacca cccatcccca cttgctcact gccccagccc cctggcctta ctccattcct    3600
cccgtagagc cccgagttgt ggatggtcgc tcctgtctaa tcattcaccc tcgatacaaa    3660
tgtgctttta gaacgggctc tcctgaccat cctttctcag gaagctccct gtcacctcac    3720
cttgctgtgc ttttccttat aacactggat gcctcatgaa tgcatgtcta tttgagtatt    3780
gctgtctcag cctcttagag tgtaagcctt ttgaggccag ggagcctgcc tgtcttactc    3840
attgccgtat ctccagcaca taggaggcag atgaagacga actgcagact cttagacaag    3900
tcttctctgt taagttttaa cttacgtaag tcatacatga ataatacatg aatctgttct    3960
caagatatta aagcagtctg gaataccatc agccgtcact gaagtcagtt gggatatttg    4020
tgtggtgatg cacctgagta aggggtgccc agatatacca gatctcccca gcagaggctc    4080
aacagaaatc cgtccatgtt gaagcggtga caaacattcc ttacaatctg gagtctttgt    4140
ttttctctct ctctaaaaga aatgtttggt atattaacca ttgattttcc cttaattgct    4200
gggggaccag gcctgaagct ctgaagaacc cctgaaacca tgaattggcc attcttattc    4260
tggaagatgc aatttggggg gtttgcatgc accaaggttt tgagggttta tgtcgttata    4320
atagcttttt ccccccagtc tccctgtcat ggcatttaca acagctttac aagatgtaat    4380
tcatataaca gtcacccatt taaagtgtat cctccagtgg ttttagtat attcattgag    4440 ttttgtcatt agcaccacag tcagttctag aacattctca tcacccatat ttacatttat    4500
ttttaataac tctcatgtgt aagctgagtg ttttaaactt tagaaacttc tgggggggtgc    4560 tgaacttgat aaaaatattc agtatacaag tgttctttat agttcactca tcattttcat    4620
```

-continued

```
agaattaggg ttttaaaatt agaaagtaat tcaggccatt tccatctcct gtccctcaaa    4680
tcccagctca gttttgggat gaggtgtcaa gtataagttt gtaagtatgc cagtcatttg    4740
cacggctaag agaaacatct agagaagtct atatacgact tgcttaaagc tgaatgttga    4800
tttactgttc acatgatttg ggcgatttta gtcactggga ctgagctaat ggagttgaag    4860
cattgttgcg ggcattgtac ctccagacca gtgtgtaata caaagagttc ttgcagacgt    4920
aggacagaat tggagaaaca gcttctaaca gtgggaagac tctcagtaca accaagctat    4980
tccttacctt tctgatttct gaactttttt ccatgtgaca cctgctgctt tgaaggcact    5040
aaaataacag aagcagatag agcagaaatc ctcactcaga tcttcctcct tcctacctgt    5100
ataacagttt gtggcttgcc ttgtctgttt tgtgtgtttc gttacgcgta tgtgagtatg    5160
tgcacgtgat ttccagaaag gagaagcgca cgatactgcc cgtgctctgt gactcctgag    5220
tgcatgcttc ctctgcattt gggctcctag gtcggcctcg tcctgtggac gttgcccctt    5280
gtttcgtgcc atccacacat tcctgatgcc cccctgctct actctttctc cagagtactt    5340
tttccaaaca tgtgatttgc acatttgtta tgtttattgt ttgttttcca cttctagaag    5400
tgtgccgcta ggcaggaatg tttgatttct tcactgatga tcccagatct ctagaaccct    5460
gccttgcctg tagagggtgc ttggtaaatg tgctctgaat gaatggctcc atgatcctcg    5520
tttctaagag ctagcactat ttctcactta gtcctggttg gacacaggtt ccctggaaca    5580
gtgctgtcgt ggttatcttc tcacgtgtct ttgtttctga acttgaaacg cttttgagtt    5640
ttttattgtt tttgttcttc ctcattagtt tgagtcccct gcagataggc tttcattttg    5700
tccagtcacc tgttcaggag ccctgagggc cttggcccat gtctgcaggt aactggtttt    5760 tttatttta ttttttatt ttgagatgaa gtctcgctct gtcaccaggc tggagtgcag    5820
cggtgcgatc tcagctcact gcaacctccg cctcctgcgt tcaagcgatt ctcctgcctc    5880
agccttccga gtaactggga ctataggcac gtgccaccac gcccggctaa ttttttgtat    5940
ttttagtaga cacggggttt caccatatta gccaggatgg tctcgatctc ctgacctcgt    6000
gatccgcctg cctgggcctc ccaaagtgct gggattacag gtgtgagcca ccgcgcccag    6060
ccctgcaggt aactgttaat gtaggaagtg ctgcctctgg gcaccttggc cccagggttc    6120
attagcagat gccctggtgg gttttgttg gctgtgatga gaagtgcttc tgttcccct    6180 ccaccacact cctgcaactg tttaaacagt ggctgtgacc ccctgagatg atccagggtt    6240
tcaaggcgtg cacatgtctg tgtttcggtt ttcagaagta tcaccttggg gtgactctca    6300
acctacatgg attttcaaag atttattcaa tgtgtttttc agaaagtgtt gtgaagagcg    6360 aagactttc gctcccagct tatatggatc ggcgtgacca ccccttgccg gaggtggccc    6420
atgtcaagca cctgtctgcc agccagaagg cactgaagga gaaggagaag gcctcctgga    6480
gcagcctctc catggatgag aaagtcgagt gtgggtattg aagggaccca caggcgcgcc    6540
cagcagctct cggaagcgtg tgtgtgacag agcctctgct cacttctggg cctactgtct    6600
agagagcagt cttgcacagg agggttgctc tgctgggttt cggggtcact gtgccagggc    6660
cccagtttat gtgctcacca gtcacttagc tctgccagct gacaggatct tttgctaggc    6720 cccttctct gtgctgagtg gaggtagcct ctcagcatat ctgctgggta agacatagtt    6780
aactgtaaat tattgaaaga aactcagcaa aatgcatagt gtttggtatg aaaggggcag    6840
aaaaataaca agattaaata gaccctaata ctgtaattca agtaagaaat aattttgcag    6900
ttttaatttg cacctgaagc gaactgtatg cattttcttc cttccttgcc ctgtcacatg    6960
cctgcgtggg cacgtgtgtg cacgtatgtg cgtgaacatg atgtggcctg ggttggtgta    7020
```

```
tccttcagct ctgtgtttcc tccttcacaa gtgtggtttt ggggagaagt ggttgaatgt    7080
tgcagaggag ggagctgctg acctttgtgc ctgtaaatgg ctgtcctctc tgccccagt     7140 gtatcgcatt aagttcaagg agagctttgc tgagatgaac aggggctcga acgagtggaa    7200
gacggttgtg ggcggtgcca tgttcttcat cggtttcacc gcgctcgtta tcatgtggca    7260
gaagcactat ggtgagtaga gagggaggaa ggcatgggcg cctggactgg ggctccagcc    7320
tgcagtgccc attggtgggc tgtggggac ctccatacct tgaggctatg agatagggac     7380
tgcattccag agttcatctc aggattgttt ccaggcctta gtgacctgga gaactgaagt    7440
cgtgggaggt tagtttataa gccagcatct gattattcat agccatgctt gttgggtggt    7500 gaaatacct aactactttg tacagcacac cacgttttca gtagcaattt atgtgctcac      7560
cagtcactta gcaaaagatg acttcgtgaa ggttcgagca aggataaggg gactcattca    7620
tttaatgact gtctcgactg ttgtgaggac tgcatctcaa cagccagcat ctgggggtcc    7680
cgacctgata gtttgtgtgt gggcattgcc gggttgctcg ctcgtggtaa tgactcttcc    7740
ccgaggttct ttctgtccag gcagaacagg cattttttgca ttctgaatag gtatattctc   7800
gtacttttgg tttgaatgtg gatgtgggtt aataacgacc cgaatctatt tgatcttcca    7860
ggtcaccttg ggctctgttt gtcagatcct gttatccata gcctttagag aggaccttct    7920
gcttttagct tattttgttg ctaactttt acaaacaaag ggctaatttt aaaatgtcag      7980
tgttgtcagt ggtcagaaac cgtgtgtttg agcgggtgtt gagtggcagg tggctctgct    8040
gacctggtgg ctggtgtgtc gggaggattt aacctgtgtg agggattggc ctagaaacaa    8100
cctgttgaga tagtcttgcc ccataacctg tctcacaccg tagtgtacgg cccctcccg     8160 caaagctttg acaaagagtg ggtggccaag cagaccaaga ggatgctgga catgaaggtg    8220 aacccccatcc agggcttagc ctccaagtgg gactacgaaa agaacgagtg aagaagtga    8280 gagatgctgg cctgcgcctg cacctgcgcc tggctctgtc accgccatgc aactccatgc    8340
ctatttactg gaaacctgtt atgccaaaca gttgtaccac tgctaataaa tgaccagttt    8400
acctgaaacc ctttgtgatc agttcttaa tgatacctaa atgaaagcta attaaaacaa     8460
taggtttctc ccaagggtct ggagtaaata tattttgggt gcaaatgaaa tggcaaaaat    8520
ctagtatctt aaattgtata agggacatt atataaaaac tgaaaatata gaattc         8576
```

<210> SEQ ID NO 6
<211> LENGTH: 683
<212> TYPE: DNA
<213> ORGANISM: Homo sapiens

<400> SEQUENCE: 6

```
caggtccctc cgcagcgggt tctcagttgc tcgctgggca gacccaggtc gcgctcccac     60
tgccgagccc gcgagatgct ccccagagct gcctggagct tggtgctgag gaaaggtgga   120
ggtggaagac gagggatgca cagctcagaa ggcaccaccc gtggtggggg aagatgtcc    180 ccctacacca actgctatgc ccagcgctac taccccatgc cagaagagcc cttctgcaca   240
gaactcaacg ctgaggagca ggccctgaag gagaaggaga agggaagctg acccagctg    300 acccacgccg aaaaggtggc cttgtaccgg ctccagttca tgagaccctt gcggagatg    360 aaccgtcgct ccaatgagtg gaagacagtg atgggttgtg tcttcttctt cattggattc   420
gcagctctgg tgatttggtg gcagcgggtc tacgtatttc ctccaaagcc gatcaccttg   480
acggacgagc ggaaagccca gcagctgcag cgcatgctgg acatgaaggt gaatcctgtg   540
```

```
cagggcctgg cctcccactg ggactatgag aagaagcagt ggaagaagtg acttgcatcc      600
ccagctgtct ccctgaggct ccgccctggc tgggacctct ggcggcccct cccctcccct      660
gcccttaacc ccagtaaagc tcc                                              683

<210> SEQ ID NO 7
<211> LENGTH: 171
<212> TYPE: PRT
<213> ORGANISM: Homo sapiens

<400> SEQUENCE: 7

Met Leu Pro Arg Ala Ala Trp Ser Leu Val Leu Arg Lys Gly Gly Gly
 1               5                  10                  15

Gly Arg Arg Gly Met His Ser Ser Glu Gly Thr Thr Arg Gly Gly Gly
                20                  25                  30

Lys Met Ser Pro Tyr Thr Asn Cys Tyr Ala Gln Arg Tyr Tyr Pro Met
            35                  40                  45

Pro Glu Glu Pro Phe Cys Thr Glu Leu Asn Ala Glu Glu Gln Ala Leu
        50                  55                  60

Lys Glu Lys Glu Lys Gly Ser Trp Thr Gln Leu Thr His Ala Glu Lys
65                  70                  75                  80

Val Ala Leu Tyr Arg Leu Gln Phe Asn Glu Thr Phe Ala Glu Met Asn
                85                  90                  95

Arg Arg Ser Asn Glu Trp Lys Thr Val Met Gly Cys Val Phe Phe Phe
               100                 105                 110

Ile Gly Phe Ala Ala Leu Val Ile Trp Trp Gln Arg Val Tyr Val Phe
            115                 120                 125

Pro Pro Lys Pro Ile Thr Leu Thr Asp Glu Arg Lys Ala Gln Gln Leu
        130                 135                 140

Gln Arg Met Leu Asp Met Lys Val Asn Pro Val Gln Gly Leu Ala Ser
145                 150                 155                 160

His Trp Asp Tyr Glu Lys Lys Gln Trp Lys Lys
                165                 170

<210> SEQ ID NO 8
<211> LENGTH: 704
<212> TYPE: DNA
<213> ORGANISM: Rattus norvegicus

<400> SEQUENCE: 8
ccgccgtctt cagcttgcaa ctatgttttc cagagctacc cggagtctgg taatgaagac      60
aggaggactc agaactcaag ggacacacag cccaggaagt gctgctagca gcagccagcg     120
gaggatgacc cctatgttga ctgctatgc tcagcgctcc tatcccatgc cggatgagcc      180
ttactgcaca gagctcagcg aggagcagcg ggccctgaag gagaaagaga agggcagctg     240
ggctcagctg agccaagcag agaaggtggc cttgtaccgg ctccagttcc acgagacctt     300
cgcagagatg aaccatcgct ccaacgaatg gaagacagta atgggctgcg tcttcttctt     360
cattggattc acggctctgg tgatttggtg gcagcgggtc tatgtgttcc ctaagaaggt     420
tgtcaccctg acggaagaac ggaaagccca gcagctccag cgcctcctgg acatgaagag     480 caacccccata cagggcctgt ctgcccactg ggattacgag aagaaagagt ggaaaaagtg     540
accaacatca cagtctgctg cctgcccttg caaaccgatt ccgcttccgc agcctaggag     600
accctcctct cctctcttct cctcccttcc cctcccccac ctcctgtctt gtctcctcca     660
ttcccttctg ctccaataaa agcagcctgc attgttctgc ctgc                      704
```

<210> SEQ ID NO 9
<211> LENGTH: 172
<212> TYPE: PRT
<213> ORGANISM: Rattus norvegicus

<400> SEQUENCE: 9

Met Phe Ser Arg Ala Thr Arg Ser Leu Val Met Lys Thr Gly Gly Leu
1               5                   10                  15

Arg Thr Gln Gly Thr His Ser Pro Gly Ser Ala Ala Ser Ser Ser Gln
            20                  25                  30

Arg Arg Met Thr Pro Tyr Val Asp Cys Tyr Ala Gln Arg Ser Tyr Pro
        35                  40                  45

Met Pro Asp Glu Pro Tyr Cys Thr Glu Leu Ser Glu Glu Gln Arg Ala
    50                  55                  60

Leu Lys Glu Lys Glu Lys Gly Ser Trp Ala Gln Leu Ser Gln Ala Glu
65                  70                  75                  80

Lys Val Ala Leu Tyr Arg Leu Gln Phe His Glu Thr Phe Ala Glu Met
                85                  90                  95

Asn His Arg Ser Asn Glu Trp Lys Thr Val Met Gly Cys Val Phe Phe
            100                 105                 110

Phe Ile Gly Phe Thr Ala Leu Val Ile Trp Trp Gln Arg Val Tyr Val
        115                 120                 125

Phe Pro Lys Lys Val Val Thr Leu Thr Glu Glu Arg Lys Ala Gln Gln
    130                 135                 140

Leu Gln Arg Leu Leu Asp Met Lys Ser Asn Pro Ile Gln Gly Leu Ser
145                 150                 155                 160

Ala His Trp Asp Tyr Glu Lys Lys Glu Trp Lys Lys
                165                 170

<210> SEQ ID NO 10
<211> LENGTH: 727
<212> TYPE: DNA
<213> ORGANISM: Mus musculus

<400> SEQUENCE: 10
agtcactcag cagggcagct ctggatagtt ccgccgcctc cagcttgcaa ttatgttttc      60
cagagctgcc cggagtctgg taatgaggac aggactcaga actagaggga cagggacaca     120
cagcccagga gatgctgctg gcagccagag gaggatgacc ccctacgttg actgctacgc     180
ccagcgctcc tatcccatgc cggatgagcc cttctgcaca gagctcagcg aggagcagcg     240
ggccctgaag gagaaagaga agggcagctg gacccagctg agccaagcag agaaggtggc     300
cttgtaccgg ctccagttcc atgaaacctt cgcagagatg aaccatcgct ccaacgaatg     360
gaagacagtg atgggctgcg tcttcttctt cattggattc acggctctgg tgatttggtg     420
gcagcgagtc tatgtgttcc ctaagaaggt tgtcaccctg acggaagaac ggaaagccca     480
acagctccag cgcctcctgg acatgaagag caaccccata cagggcctgg ctgcccactg     540
ggattatgaa aagaaggagt ggaaaaagtg accaacgtcc cacgtctgcc gccagcccct     600
gcaaactgct tctgcagccc aggagacaat catcccctcc cctcccctcc cttccctcct     660
cctcctgagt cctgtctcca ctcccttctc caataaaagc agcctgcttt gttctgcttg     720
caaactc                                                                727

<210> SEQ ID NO 11
<211> LENGTH: 172
<212> TYPE: PRT

<213> ORGANISM: Mus musculus

<400> SEQUENCE: 11

Met Phe Ser Arg Ala Ala Arg Ser Leu Val Met Arg Thr Gly Leu Arg
1               5                   10                  15

Thr Arg Gly Thr Gly Thr His Ser Pro Gly Asp Ala Ala Gly Ser Gln
            20                  25                  30

Arg Arg Met Thr Pro Tyr Val Asp Cys Tyr Ala Gln Arg Ser Tyr Pro
        35                  40                  45

Met Pro Asp Glu Pro Phe Cys Thr Glu Leu Ser Glu Glu Gln Arg Ala
    50                  55                  60

Leu Lys Glu Lys Glu Lys Gly Ser Trp Thr Gln Leu Ser Gln Ala Glu
65                  70                  75                  80

Lys Val Ala Leu Tyr Arg Leu Gln Phe His Thr Phe Ala Glu Met
                85                  90                  95

Asn His Arg Ser Asn Glu Trp Lys Thr Val Met Gly Cys Val Phe Phe
                100                 105                 110

Phe Ile Gly Phe Thr Ala Leu Val Ile Trp Trp Gln Arg Val Tyr Val
            115                 120                 125

Phe Pro Lys Lys Val Val Thr Leu Thr Glu Glu Arg Lys Ala Gln Gln
        130                 135                 140

Leu Gln Arg Leu Leu Asp Met Lys Ser Asn Pro Ile Gln Gly Leu Ala
145                 150                 155                 160

Ala His Trp Asp Tyr Glu Lys Lys Glu Trp Lys Lys
                165                 170

<210> SEQ ID NO 12
<211> LENGTH: 169
<212> TYPE: PRT
<213> ORGANISM: Homo sapiens

<400> SEQUENCE: 12

Met Leu Ala Thr Arg Val Phe Ser Leu Val Gly Lys Arg Ala Ile Ser
1               5                   10                  15

Thr Ser Val Cys Val Arg Ala His Glu Ser Val Val Lys Ser Glu Asp
            20                  25                  30

Phe Ser Leu Pro Ala Tyr Met Asp Arg Arg Asp His Pro Leu Pro Glu
        35                  40                  45

Val Ala His Val Lys His Leu Ser Ala Ser Gln Lys Ala Leu Lys Glu
    50                  55                  60

Lys Glu Lys Ala Ser Trp Ser Ser Leu Ser Met Asp Glu Lys Val Glu
65                  70                  75                  80

Leu Tyr Arg Ile Lys Phe Lys Glu Ser Phe Ala Glu Met Asn Arg Gly
                85                  90                  95

Ser Asn Glu Trp Lys Thr Val Val Gly Gly Ala Met Phe Phe Ile Gly
                100                 105                 110

Phe Thr Ala Leu Val Ile Met Trp Gln Lys His Tyr Val Tyr Gly Pro
            115                 120                 125

Leu Pro Gln Ser Phe Asp Lys Glu Trp Val Ala Lys Gln Thr Lys Arg
        130                 135                 140

Met Leu Asp Met Lys Val Asn Pro Ile Gln Gly Leu Ala Ser Lys Trp
145                 150                 155                 160

Asp Tyr Glu Lys Asn Glu Trp Lys Lys
                165

<210> SEQ ID NO 13
<211> LENGTH: 169
<212> TYPE: PRT
<213> ORGANISM: Mus musculus

<400> SEQUENCE: 13

```
Met Leu Ala Ser Arg Ala Leu Ser Leu Ile Gly Lys Arg Ala Ile Ser
 1               5                  10                  15

Thr Ser Val Cys Leu Arg Ala His Gly Ser Val Val Lys Ser Glu Asp
            20                  25                  30

Tyr Ala Leu Pro Thr Tyr Ala Asp Arg Arg Asp Tyr Pro Leu Pro Asp
        35                  40                  45

Val Ala His Val Thr Met Leu Ser Ala Ser Gln Lys Ala Leu Lys Glu
    50                  55                  60

Lys Glu Lys Ala Asp Trp Ser Ser Leu Ser Arg Asp Glu Lys Val Gln
65                  70                  75                  80

Leu Tyr Arg Ile Gln Phe Asn Glu Ser Phe Ala Glu Met Asn Arg Gly
                85                  90                  95

Thr Asn Glu Trp Lys Thr Val Val Gly Met Ala Met Phe Phe Ile Gly
            100                 105                 110

Phe Thr Ala Leu Val Leu Ile Trp Glu Lys Ser Tyr Val Tyr Gly Pro
        115                 120                 125

Ile Pro His Thr Phe Asp Arg Asp Trp Val Ala Met Gln Thr Lys Arg
    130                 135                 140

Met Leu Asp Met Lys Ala Asn Pro Ile Gln Gly Phe Ser Ala Lys Trp
145                 150                 155                 160

Asp Tyr Asp Lys Asn Glu Trp Lys Lys
                165
```

<210> SEQ ID NO 14
<211> LENGTH: 169
<212> TYPE: PRT
<213> ORGANISM: Rattus norvegicus

<400> SEQUENCE: 14

```
Met Leu Ala Thr Arg Ala Leu Ser Leu Ile Gly Lys Arg Ala Ile Ser
 1               5                  10                  15

Thr Ser Val Cys Leu Arg Ala His Gly Ser Val Val Lys Ser Glu Asp
            20                  25                  30

Tyr Ala Leu Pro Ser Tyr Val Asp Arg Arg Asp Tyr Pro Leu Pro Asp
        35                  40                  45

Val Ala His Val Lys Leu Leu Ser Ala Ser Gln Lys Ala Leu Lys Glu
    50                  55                  60

Lys Glu Lys Ala Asp Trp Ser Ser Leu Ser Arg Asp Glu Lys Val Gln
65                  70                  75                  80

Leu Tyr Arg Ile Gln Phe Asn Glu Ser Phe Ala Glu Met Asn Lys Gly
                85                  90                  95

Thr Asn Glu Trp Lys Thr Val Val Gly Leu Ala Met Phe Phe Ile Gly
            100                 105                 110

Phe Thr Ala Leu Val Leu Ile Trp Glu Lys Ser Tyr Val Tyr Gly Pro
        115                 120                 125

Ile Pro His Thr Phe Asp Arg Asp Trp Val Ala Met Gln Thr Lys Arg
    130                 135                 140

Met Leu Asp Met Lys Val Asn Pro Ile Gln Gly Phe Ser Ala Lys Trp
145                 150                 155                 160

Asp Tyr Asn Lys Asn Glu Trp Lys Lys
```

-continued

```
                                 165

<210> SEQ ID NO 15
<211> LENGTH: 170
<212> TYPE: PRT
<213> ORGANISM: Bos taurus

<400> SEQUENCE: 15

Met Leu Ala Thr Arg Val Phe Ser Leu Ile Gly Arg Arg Ala Ile Ser
1               5                   10                  15

Thr Ser Val Cys Val Arg Ala His Gly Ser Val Val Lys Ser Glu Asp
            20                  25                  30

Tyr Ala Leu Pro Ser Tyr Val Asp Arg Arg Asp Tyr Pro Leu Pro Asp
        35                  40                  45

Val Ala His Val Lys Asn Leu Ser Ala Ser Gln Lys Ala Leu Lys Glu
    50                  55                  60

Lys Glu Lys Ala Ser Asp Trp Ser Ser Leu Ser Ile Asp Glu Lys Val
65                  70                  75                  80

Glu Leu Tyr Arg Leu Lys Phe Lys Glu Ser Phe Ala Glu Met Asn Arg
                85                  90                  95

Ser Thr Asn Glu Trp Lys Thr Val Val Gly Ala Ala Met Phe Phe Ile
            100                 105                 110

Gly Phe Thr Ala Leu Leu Leu Ile Trp Glu Lys His Tyr Val Tyr Gly
        115                 120                 125

Pro Ile Pro His Thr Phe Glu Glu Glu Trp Val Ala Lys Gln Thr Lys
    130                 135                 140

Arg Met Leu Asp Met Lys Val Ala Pro Ile Gln Gly Phe Ser Ala Lys
145                 150                 155                 160

Trp Asp Tyr Asp Lys Asn Glu Trp Lys Lys
                165                 170
```

METHOD TO DETECT LUNG CANCER

RELATED APPLICATION

This application claims priority to U.S. Provisional Patent Application Ser. No. 60/677,776, which was filed on May 4, 2005 and which is incorporated herein by reference.

FIELD OF THE INVENTION

Certain embodiments of the present invention relate to methods for detecting lung cancer.

BACKGROUND OF THE INVENTION

Lung cancer is the leading cause of cancer death and accounts for nearly 30% of all cancer deaths in the United States, and there is an increasing incidence of lung cancer in the world. The overall 5-year survival rate of patients with lung cancer has not improved significantly over the last 30 years and remains at only 10-15% in the United States. The prognosis of patients with lung cancer depends in large part on the stage of presentation when the lung cancer is diagnosed. Thus, early detection of lung cancer in conjunction with early treatment would be expected to significantly reduce mortality from lung cancer.

Accordingly, there is a need for methods for detecting lung cancer, e.g., methods for detecting lung cancer at an early stage of presentation.

SUMMARY OF CERTAIN EMBODIMENTS THE INVENTION

It has been discovered that the COX4-2 isoform of cytochrome c oxidase (COX) is a highly significant marker for lung cancer as downregulation of the COX4-2 gene is indicative of the presence of lung cancer.

Accordingly, certain embodiments of the present invention provide a method for detecting the presence of lung cancer in a first biological sample, including determining the level of isoform 2 of subunit 4 of cytochrome c oxidase (COX4-2) in the first biological sample, wherein a lower level of COX4-2 in the first biological sample as compared to the level of COX4-2 in a second biological sample that does not include lung cancer indicates the presence of lung cancer in the first biological sample.

Certain embodiments of the present invention provide a method for screening a subject at an elevated risk for developing lung cancer, including determining the level of isoform 2 of subunit 4 of cytochrome c oxidase (COX4-2) in a biological sample from the subject, wherein a lower level of COX4-2 in the sample as compared to the level of COX4-2 in a biological sample that does not include lung cancer indicates the that the subject has lung cancer.

Certain embodiments of the present invention provide a method for identifying and treating lung cancer in a subject, including determining the level of isoform 2 of subunit 4 of cytochrome c oxidase (COX4-2) in a biological sample from the subject, wherein a lower level of COX4-2 in the sample as compared to the level of COX4-2 in a biological sample that does not include lung cancer indicates the that the subject has lung cancer, and administering a treatment for lung cancer to the patient.

Certain embodiments of the present invention provide a method for determining whether a subject has lung cancer, including determining the level of isoform 2 of subunit 4 of cytochrome c oxidase (COX4-2) in a biological sample from the subject, wherein a lower level of COX4-2 in the sample as compared to the level of COX4-2 in a biological sample that does not include lung cancer indicates the that the subject has developed lung cancer.

In certain embodiments of the invention, the methods may further include determining the level of isoform 1 of subunit 4 of cytochrome c oxidase (COX4-1) in a sample and comparing the level of COX4-2 to COX4-1, wherein a lower ration of COX4-1 to COX4-2 indicates the presence of lung cancer in the sample.

DETAILED DESCRIPTION OF CERTAIN EMBODIMENTS OF THE INVENTION

Figure 1:
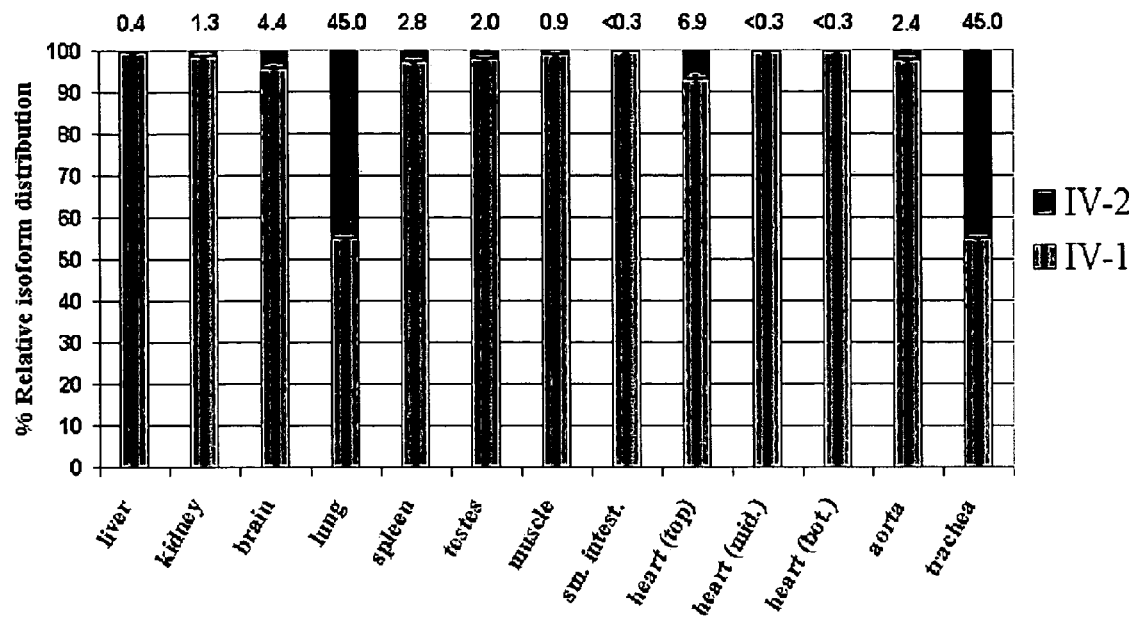
FIG. 1. Relative quantitative PCR of cytochrome c oxidase subunit isoforms 4-1 and 4-2 reveals strong expression in lung and trachea.

COX is the rate-limiting enzyme of the mitochondrial respiratory chain that provides humans with the vast majority of their energy requirements. Consistent with its position as a pacemaker of aerobic metabolism, the activity of COX is tightly regulated through several means, including tissue-specific isoforms. As described herein, it is this form of regulation that is directly relevant to lung cancer because of the existence of two isoforms of subunit 4 of COX.

COX 4 is the key regulatory subunit of COX that adjusts enzyme activity to meet cellular energy demand. The gene encoding the lung-specific isoform, COX4-2, is switched on after birth and is expressed in all cell types of the lung. Presented herein are studies that indicate that expression of the COX4-2 gene is dramatically downregulated in lung cancer, whereas expression of the somatic isoform of the gene, COX4-1, is at normal levels. This finding is consistent for various types of lung cancer and lung cancer cell lines, including a cell culture model simulating the carcinogenesis process in vivo, where COX4-2 is downregulated from the earliest stages.

```
The genomic DNA sequence for human COX4-1 is as follows (SEQ ID NO:5):

1 gagctccggg gtgcccgagt accgacagcc aaagaagcat ttacactttg ccagataagg 61 aatcggctct gcgaaggtgc gaagaaccaa atcctagcga ttaatgtccc aacaacgtga 121 acacttcctg caactcgaaa tcctcaaggg aaactctgtc gaatccccac caagtgaacg
```

-continued

```
 181 atgacttgtt tctacaaagg ctactgattt caggaaacta acgtataact cgtcgcctta
 241 aagtgcctct aaaagcatcc acgacggtta aaagtcgctg ctactacggg acgctattta
 301 ttcagcgcca agacccaagc gccatcgtgg atcaccccat tcctggccac ggcaaccctta
 361 gggagcgggt cctaggagcc tgctggaggg cgaccgctgg gccagcttcc tctctgctga
 421 ctgaggggag gccaggctgc ctgcaagggg aaggggccct ttccgcgctt accagggtga
 481 gagccacctc cagcatgggg gcgagggcca gggtgccgtg aagaggggg atgcagtcca
 541 cgaagagggt gtggtgggcg ccggggccgc ccaggggag gtgctcctta cgcggcttct
 601 gcttctcggc caccaggagc ccgttgacgg cgcagtgcgg gtacttggcg ccgtgcagca
 661 ccatcttgca gtaggcctgg gtggtcagtt tcaccccggg catgctgacc cgggagggcc
 721 ccggaggccc ctgggcgcgc ggctgaggcc tggacccgct gcctggccgc gcggcgcctc
 781 agccgagaag cgggacgagg cggcggcgat tgatggcgcg gccgcgggct ggcggggac
 841 ccttcaggcc cggccccgtt tgggcctcgg ctcctggaaa agcgactcgc gcctctggga
 901 agccgcagcc ccagactcca gtcgcgcttc tcgcccggcg ccgccggaaa gcagcctctc
 961 caacgcctgc cggaaagcag cccggcccgg cattttacga cgttcgcagc gctacccttt
1021 tccgctccac ggtgacctcc gtgcggcgg gtgcgggcgg agtcttcctc gatcccgtgg
1081 tgctccgcgg cgcggccttg ctctcttccg gtcgcgggac accgggtgta gagggcggtc
1141 gcggcgggca gtggcggcag gtgagacagg aggtggccgg tgcggcgccg ccaggccggg
1201 ccgggtcggg gggccgggag ccatcaagtc tgcacgtccg cagcctggcc gctcggcttc
1261 agcaggaagc accgaatggg cctcggagcc aggtgacatt gaggccggcc cgtgggact
1321 ccgggctcgg tggctccagg ctcgggggc cgccccgaag tgcccggtcc atcttacccg
1381 gtctcgcagc ggctgcggac cggcctcggg cactgacctt ggagcgcccg ctggccgagg
1441 gctcaggctg cggggaggcg ggcccgcgct ctgtgcctgc agcctccgcc cttgctcctt
1501 caaaaggtcc ctgtgcaacc cctcccgggt tttgcgggac tcccgggcgg cgctcggctt
1561 tccagcctgg aaggcgccta ttgtttgctc acgcaagggc taggcccaag gagagaagct
1621 agacgcgggc gttcagccct gacgtcatgc ttgtttattc tgccccaagg agggtatttc
1681 cccacatcac tctcaccagt cctccgaagg gtcgatttaa agggggccgt gtaaggttga
1741 tgggcctgaa tagaggaggg cccgggtgag gggggtctc ataggttttc cgctctcctc
1801 agggattgga aattgatcgg ggctgtgttg gcagccttct ccaatttccc cttctagtct
1861 atgtacaggc ggtattaggt tttaaaacac tcagttgaat gtgatgcgtg ccacggtccc
1921 tgtgagctgt caccctcccc caccgctccc tgaagaatgg agcctgtcac ggcagcacag
1981 tgctttaatg atctctagct ttttcagagt caccttgtta gcattttttc ttcttgcctt
2041 tttttgtttg agacggactc ttgctctggt tgcccaggct ggggtgcagt ggtgcggtct
2101 cggctcactg cagtctctac ctcccgggtt caagcgattc ttctacctca gcctcccaag
2161 tagcggggat tacgggcgcc cactaccatg cccggctaat ttttgtattg ttagtagaga
2221 cgggatttca ccatgttggc caggctggtc ttgaacccct gacctcaggt gatctgtccg
2281 cctcggcctc ccaaagtgct ggaattaccg gcgtgagcca ccgcgccgg cctctccttg
2341 ttttttttaaa aagaccaatg ttctgttaat tacctgaagc gcgtatatat tatggcagtt
2401 gatttataat gaagctcctt aaaagcatgc caattactaa gaaaaacctc atcctaggtc
2461 attttgtgaa ttcagagaca gtgataaaga atgatcatt tgcgttgggg agaagcaaac
2521 aaaaaaattc caaaatgctc tggggcaaaa agaagactaa ttccttgctg tttgtcctta
```

-continued

```
2581 ttcatagaga aggtgtacat tttatctttt cagaatgttg gctaccaggg tatttagcct 2641 agttggcaag cgagcaattt ccacctctgt gtgtgtacga gctcatggta agtgtgactt 2701 ttcttacttt taaataggct gaactaattt cattttgctc ctgctgtgta taaagccctg 2761 tgctggagtt ttaaagacct taattcggct cttgagggtc tttaggggag atataaatgt 2821 tctcacaggg cttggttcta gattaagaag tgtttataag tcaaattgaa tctcttctgg 2881 atctttggtt atactgatac ttccccactt acccttccct tccgttccac tttttttaagc 2941 ttcgaggatc tacccctttc aaaaagatct tctgcaccat aactgactga ccttaatgac 3001 ctccctcccc accttgcccc cacaactccc aaccatttgc atcacctctg tttacattat 3061 agaggcaatg gaaacgaaag agcctggact tcctagcctg agctgggttt tcatctcatt 3121 tctatcaagg actagctact gaagctcagg aatctctttg ctcacctgaa gtatatggac 3181 agagcttagt tctgtgtctg gcatacagca catttacttt tgcatgtatc tggcgtctat 3241 ctactttgta ccagacactg ttaggcaccg agaagaaaaa gaatatgaaa tacacacact 3301 ttccaggagg ctgtttgcaa tctgaagagg gacggatggg tgaagacagt gttttattaa 3361 gagatggctc ctgggtagaa gcatttagcc cgatgtgggt ttcagggaag gcttctggag 3421 gaaactctcc agggtctttt cattgcctta gtagagtcta caccctgcct ggttagagct 3481 ggtcttgcct gcctttccga tcttattact gactgttgta ctcaaaaccc aaaaactacc 3541 atcagaacca cccatcccca cttgctcact gccccagccc cctggcctta ctccattcct 3601 cccgtagagc cccgagttgt ggatggtcgc tcctgtctaa tcattcaccc tcgatacaaa 3661 tgtgcttttta gaacgggctc tcctgaccat cctttctcag gaagctccct gtcacctcac 3721 cttgctgtgc ttttccttat aacactggat gcctcatgaa tgcatgtcta tttgagtatt 3781 gctgtctcag cctcttagag tgtaagcctt ttgaggccag ggagcctgcc tgtcttactc 3841 attgccgtat ctccagcaca taggaggcag atgaagacga actgcagact cttagacaag 3901 tcttctctgt taagttttaa cttacgtaag tcatacatga ataatacatg aatctgttct 3961 caagatatta aagcagtctg gaataccatc agccgtcact gaagtcagtt gggatatttg 4021 tgtggtgatg cacctgagta aggggtgccc agatatacca gatctcccca gcagaggctc 4081 aacagaaatc cgtccatgtt gaagcggtga caaacattcc ttacaatctg gagtctttgt 4141 ttttctctct ctctaaaaga aatgtttggt atattaacca ttgattttcc cttaattgct 4201 gggggaccag gcctgaagct ctgaagaacc cctgaaacca tgaattggcc attcttattc 4261 tggaagatgc aatttggggg gtttgcatgc accaaggttt tgagggttta tgtcgttata 4321 atagcttttt ccccccagtc tccctgtcat ggcatttaca acagctttac aagatgtaat 4381 tcatataaca gtcacccatt taaagtgtat cctccagtgg ttttttagtat attcattgag 4441 ttttgtcatt agcaccacag tcagttctag aacattctca tcacccatat ttacatttat 4501 ttttaataac tctcatgtgt aagctgagtg ttttaaactt tagaaacttc tggggggtgc 4561 tgaacttgat aaaaatattc agtatacaag tgttctttat agttcactca tcatttttcat 4621 agaattaggg ttttaaaatt agaaagtaat tcaggccatt tccatctcct gtccctcaaa 4681 tcccagctca gttttgggat gaggtgtcaa gtataagttt gtaagtatgc cagtcatttg 4741 cacggctaag agaaacatct agagaagtct atatacgact tgcttaaagc tgaatgttga 4801 tttactgttc acatgatttg ggcgatttta gtcactggga ctgagctaat ggagttgaag 4861 cattgttgcg ggcattgtac ctccagacca gtgtgtaata caaagagttc ttgcagacgt 4921 aggacagaat tggagaaaca gcttctaaca gtgggaagac tctcagtaca accaagctat
```

-continued

```
4981 tccttacctt tctgatttct gaactttttt ccatgtgaca cctgctgctt tgaaggcact
5041 aaaataacag aagcagatag agcagaaatc ctcactcaga tcttcctcct tcctacctgt
5101 ataacagttt gtggcttgcc ttgtctgttt tgtgtgtttc gttacgcgta tgtgagtatg
5161 tgcacgtgat ttccagaaag gagaagcgca cgatactgcc cgtgctctgt gactcctgag
5221 tgcatgcttc ctctgcattt gggctcctag gtcggcctcg tcctgtggac gttgcccctt
5281 gtttcgtgcc atccacacat tcctgatgcc ccctgctct actctttctc cagagtactt
5341 tttccaaaca tgtgatttgc acatttgtta tgtttattgt ttgttttcca cttctagaag
5401 tgtgccgcta ggcaggaatg tttgatttct tcactgatga tcccagatct ctagaaccct
5461 gccttgcctg tagagggtgc ttggtaaatg tgctctgaat gaatggctcc atgatcctcg
5521 tttctaagag ctagcactat ttctcactta gtcctggttg gacacaggtt ccctggaaca
5581 gtgctgtcgt ggttatcttc tcacgtgtct ttgtttctga acttgaaacg cttttgagtt
5641 ttttattgtt tttgttcttc ctcattagtt tgagtcccct gcagataggc tttcattttg
5701 tccagtcacc tgttcaggag ccctgagggc cttggcccat gtctgcaggt aactggtttt
5761 ttttattttta tttttttatt ttgagatgaa gtctcgctct gtcaccaggc tggagtgcag
5821 cggtgcgatc tcagctcact gcaacctccg cctcctgcgt tcaagcgatt ctcctgcctc
5881 agccttccga gtaactggga ctataggcac gtgccaccac gcccggctaa tttttttgtat
5941 ttttagtaga cacggggttt caccatatta gccaggatgg tctcgatctc ctgacctcgt
6001 gatccgcctg cctgggcctc ccaaagtgct gggattacag gtgtgagcca ccgcgcccag
6061 ccctgcaggt aactgttaat gtaggaagtg ctgcctctgg gcaccttggc cccagggttc
6121 attagcagat gccctggtgg gttttttgttg gctgtgatga gaagtgcttc tgttccccct
6181 ccaccacact cctgcaactg tttaaacagt ggctgtgacc ccctgagatg atccagggtt
6241 tcaaggcgtg cacatgtctg tgtttcggtt ttcagaagta tcaccttggg gtgactctca
6301 acctacatgg atttttcaaag atttattcaa tgtgtttttc agaaagtgtt gtgaagagcg
6361 aagacttttc gctcccagct tatatggatc ggcgtgacca ccccttgccg gaggtggccc
6421 atgtcaagca cctgtctgcc agccagaagg cactgaagga gaaggagaag gcctcctgga
6481 gcagcctctc catggatgag aaagtcgagt gtgggtattg aagggaccca caggcgcgcc
6541 cagcagctct cggaagcgtg tgtgtgacag agcctctgct cacttctggg cctactgtct
6601 agagagcagt cttgcacagg agggttgctc tgctgggttt cggggtcact gtgccagggc
6661 cccagtttat gtgctcacca gtcacttagc tctgccagct gacaggatct tttgctaggc
6721 ccccttctct gtgctgagtg gaggtagcct ctcagcatat ctgctgggta agacatagtt
6781 aactgtaaat tattgaaaga aactcagcaa aatgcatagt gtttggtatg aaaggggcag
6841 aaaaataaca agattaaata gaccctaata ctgtaattca agtaagaaat aattttgcag
6901 ttttaatttg cacctgaagc gaactgtatg cattttcttc cttccttgcc ctgtcacatg
6961 cctgcgtggg cacgtgtgtg cacgtatgtg cgtgaacatg atgtggcctg ggttggtgta
7021 tccttcagct ctgtgtttcc tccttcacaa gtgtggtttt ggggagaagt ggttgaatgt
7081 tgcagaggag ggagctgctg acctttgtgc ctgtaaatgg ctgtcctctc tgcccccagt
7141 gtatcgcatt aagttcaagg agagctttgc tgagatgaac aggggctcga acgagtggaa
7201 gacggttgtg ggcggtgcca tgttcttcat cggtttcacc gcgctcgtta tcatgtggca
7261 gaagcactat ggtgagtaga gagggaggaa ggcatgggcg cctggactgg ggctccagcc
7321 tgcagtgccc attggtgggc tgtgggggac ctccatacct tgaggctatg agatagggac
```

-continued

```
7381 tgcattccag agttcatctc aggattgttt ccaggccttg gtgacctgga gaactgaagt 7441 cgtgggaggt tagtttataa gccagcatct gattattcat agccatgctt gttgggtggt 7501 gaaatacccct aactactttg tacagcacac cacgttttca gtagcaattt atgtgctcac 7561 cagtcactta gcaaaagatg acttcgtgaa ggttcgagca aggataaggg gactcattca 7621 tttaatgact gtctcgactg ttgtgaggac tgcatctcaa cagccagcat ctgggggtcc 7681 cgacctgata gtttgtgtgt gggcattgcc gggttgctcg ctcgtggtaa tgactcttcc 7741 ccgaggttct ttctgtccag gcagaacagg catttttgca ttctgaatag gtatattctc 7801 gtacttttgg tttgaatgtg gatgtgggtt aataacgacc cgaatctatt tgatcttcca 7861 ggtcaccttg ggctctgttt gtcagatcct gttatccata gcctttagag aggaccttct 7921 gcttttagct tattttgttg ctaactttt acaaacaaag ggctaatttt aaaatgtcag 7981 tgttgtcagt ggtcagaaac cgtgtgtttg agcgggtgtt gagtggcagg tggctctgct 8041 gacctggtgg ctggtgtgtc gggaggattt aacctgtgtg agggattggc ctagaaacaa 8101 cctgttgaga tagtcttgcc ccataacctg tctcacaccg tagtgtacgg ccccctcccg 8161 caaagctttg acaaagagtg ggtggccaag cagaccaaga ggatgctgga catgaaggtg 8221 aaccccatcc agggcttagc ctccaagtgg gactacgaaa agaacgagtg gaagaagtga 8281 gagatgctgg cctgcgcctg cacctgcgcc tggctctgtc accgccatgc aactccatgc 8341 ctatttactg gaaacctgtt atgccaaaca gttgtaccac tgctaataaa tgaccagttt 8401 acctgaaacc ctttgtgatc agttctttaa tgatacctaa atgaaagcta attaaaacaa 8461 taggtttctc ccaagggtct ggagtaaata tattttgggt gcaaatgaaa tggcaaaaat 8521 ctagtatctt aaattgtata aggggacatt atataaaaac tgaaaatata gaattc
```

The cDNA sequence for human COX4-2 is as follows (SEQ ID NO:6):

```
  1 caggtccctc cgcagcgggt tctcagttgc tcgctgggca gacccaggtc gcgctcccac 61 tgccgagccc gcgagatgct ccccagagct gcctggagct tggtgctgag gaaaggtgga 121 ggtggaagac gagggatgca cagctcagaa ggcaccaccc gtggtggggg gaagatgtcc 181 ccctacacca actgctatgc ccagcgctac tacccccatgc cagaagagcc cttctgcaca 241 gaactcaacg ctgaggagca ggccctgaag gagaaggaga agggaagctg gacccagctg 301 acccacgccg aaaaggtggc cttgtaccgg ctccagttca atgagacctt tgcggagatg 361 aaccgtcgct ccaatgagtg gaagacagtg atgggttgtg tcttcttctt cattggattc 421 gcagctctgg tgatttggtg gcagcgggtc tacgtatttc ctccaaagcc gatcaccttg 481 acggacgagc ggaaagccca gcagctgcag cgcatgctgg acatgaaggt gaatcctgtg 541 cagggcctgg cctcccactg ggactatgag aagaagcagt ggaagaagtg acttgcatcc 601 ccagctgtct ccctgaggct ccgccctggc tgggacctct gcggcccct cccctcccct 661 gcccttaacc ccagtaaagc tcc
```

The amino acid sequence for human COX4-2 is as follows (SEQ ID NO:7):

MLPRAAWSLVLRKGGGRRGMHSSEGTTRGGGKMSPYTNCYAQRYYPMPEEPFCTELNAEEQALKEKEK
GSWTQLTHAEKVALYRLQFNETFAEMNRRSNEWKTVMGCVFFFIGFAALVIWWQRVYVFPPKPITLTDE
RKAQQLQRMLDMKVNPVQGLASHWDYEKKQWKK

The cDNA sequence for rat COX4-2 is as follows (SEQ ID NO:8):

```
  1 ccgccgtctt cagcttgcaa ctatgttttc cagagctacc cggagtctgg taatgaagac 61 aggaggactc agaactcaag ggacacacag cccaggaagt gctgctagca gcagccagcg
```

-continued

```
121 gaggatgacc ccctatgttg actgctatgc tcagcgctcc tatcccatgc cggatgagcc
181 ttactgcaca gagctcagcg aggagcagcg ggccctgaag gagaaagaga agggcagctg
241 ggctcagctg agccaagcag agaaggtggc cttgtaccgg ctccagttcc acgagacctt
301 cgcagagatg aaccatcgct ccaacgaatg gaagacagta atgggctgcg tcttcttctt
361 cattggattc acggctctgg tgatttggtg gcagcgggtc tatgtgttcc ctaagaaggt
421 tgtcaccctg acggaagaac ggaaagccca gcagctccag cgcctcctgg acatgaagag
481 caaccccata cagggcctgt ctgcccactg ggattacgag aagaaagagt ggaaaaagtg
541 accaacatca cagtctgctg cctgcccttg caaaccgatt ccgcttccgc agcctaggag
601 accctcctct cctctcttct cctcccttcc cctcccccac ctcctgtctt gtctcctcca
661 ttcccttctg ctccaataaa agcagcctgc attgttctgc ctgc
```

The amino acid sequence for rat COX4-2 is as follows (SEQ ID NO:9):

MFSRATRSLVMKTGGLRTQGTHSPGSAASSSQRRMTPYVDCYAQRSYPMPDEPYCTELSEEQRALKEKE
KGSWAQLSQAEKVALYRLQFHETFAEMNHRSNEWKTVMGCVFFFIGFTALVIWWQRVYVFPKKVVTLTE
ERKAQQLQRLLDMKSNPIQGLSAHWDYEKKEWKK

The cDNA sequence for mouse COX4-2 is as follows (SEQ ID NO:10):

```
  1 agtcactcag cagggcagct ctggatagtt ccgccgcctc cagcttgcaa ttatgttttc
 61 cagagctgcc cggagtctgg taatgaggac aggactcaga actagaggga cagggacaca
121 cagcccagga gatgctgctg gcagccagag gaggatgacc ccctacgttg actgctacgc
181 ccagcgctcc tatcccatgc cggatgagcc cttctgcaca gagctcagcg aggagcagcg
241 ggccctgaag gagaaagaga agggcagctg gacccagctg agccaagcag agaaggtggc
301 cttgtaccgg ctccagttcc atgaaacctt cgcagagatg aaccatcgct ccaacgaatg
361 gaagacagtg atgggctgcg tcttcttctt cattggattc acggctctgg tgatttggtg
421 gcagcgagtc tatgtgttcc ctaagaaggt tgtcaccctg acggaagaac ggaaagccca
481 acagctccag cgcctcctgg acatgaagag caaccccata cagggcctgg ctgcccactg
541 ggattatgaa aagaaggagt ggaaaaagtg accaacgtcc cacgtctgcc gccagcccct
601 gcaaactgct tctgcagccc aggagacaat catccccctcc cctcccctcc cttccctcct
661 cctcctgagt cctgtctcca ctcccttctc caataaaagc agcctgcttt gttctgcttg
721 caaactc
```

The amino acid sequence for mouse COX4-2 is as follows (SEQ ID NO:11):

MFSRAARSLVMRTGLRTRGTGTHSPGDAAGSQRRMTPYVDCYAQRSYPMPDEPFCTELSEEQRALKEKE
KGSWTQLSQAEKVALYRLQFHETFAEMNHRSNEWKTVMGCVFFFIGFTALVIWWQRVYVFPKKVVTLTE
ERKAQQLQRLLDMKSNPIQGLAAHWDYEKKEWKK

The amino acid sequence for human COX4-1 is as follows (SEQ ID NO:12):

MLATRVFSLVGKRAISTSVCVRAHESVVKSEDFSLPAYMDRRDHPLPEVAHVKHLSASQKALKEKEKAS
WSSLSMDEKVELYRIKFKESFAEMNRGSNEWKTVVGGAMFFIGFTALVIMWQKHYVYGPLPQSFDKEWV
AKQTKRMLDMKVNPIQGLASKWDYEKNEWKK

The amino acid sequence for mouse COX4-1 is as follows (SEQ ID NO:13):

MLASRALSLIGKRAISTSVCLRAHGSVVKSEDYALPTYADRRDYPLPDVAHVTMLSASQKALKEKEKAD
WSSLSRDEKVQLYRIQFNESFAEMNRGTNEWKTVVGMANFFIGFTALVLIWEKSYVYGPIPHTFDRDWV
AMQTKRMLDMKANPIQGFSAKWDYDKNEWKK

-continued

The amino acid sequence for rat COX4-1 is as follows (SEQ ID NO:14):

MLATRALSLIGKRAISTSVCLRAHGSVVKSEDYALPSYVDRRDYPLPDVAHVKLLSASQKALKEKEKAD

WSSLSRDEKVQLYRIQFNESFAEMNKGTNEWKTVVGLAMFFIGFTALVLIWEKSYVYGPIPHTFDRDWV

AMQTKRMLDMKVNPIQGESAKWDYNKNEWKK

The amino acid sequence for cow COX4-1 is as follows (SEQ ID NO:15):

MLATRVFSLIGRRAISTSVCVRAHGSVVKSEDYALPSYVDRRDYPLPDVAHVKNLSASQKALKEKEKAS

DWSSLSIDEKVELYRLKFKESFAEMNRSTNEWKTVVGAAMFFIGFTALLLIWEKHYVYGPIPHTFEEEW

VAKQTKRMLDMKVAPIQGFSAKWDYDKNEWKK

The data presented herein thus indicates that COX4-2 is a highly significant early marker for lung cancer. The surprising finding that COX4-2 is an important lung cancer marker will be examined by using TaqMan real time PCR on lung cancers from various stages and matching controls derived from smokers. A new diagnostic assay based on probe ligation and rolling circle amplification (RCA) is also described herein, which assay will allow for the detection of COX4-2 expression, e.g., in individual cells, e.g., in sputum, saliva, and bronchoalveolar lavage (BAL) samples. COX4-1, the ubiquitously expressed paralogue, can serve as an internal standard. The use of COX4-2 as an early lung cancer marker allow for non-invasive early lung cancer detection. Such a system will be especially valuable for screening high-risk populations e.g., people who smoke, for the development of lung cancer.

As an early biomarker of the changes ensuing upon the beginning of lung cancer, COX4-2 mRNA and/or protein are useful markers for the early diagnosis of lung cancer. Moreover, the robust, non-invasive, assay described herein will be generalizable to the detection of other biomarkers using biological samples such as bronchoalveolar lavage (BAL), sputum, blood, or cell smear samples. The assay provides a novel way to easily and quickly distinguish with great specificity and ease of visualization the differential expression of two or more genes within an individual cell. The assay will provide the ease of use, specificity, and robustness important for the routine use of a diagnostic test. Until now, such tests have generally been of the in situ hybridization type, are excessively complex, lack specificity, and are time consuming. Thus, also provided are kits for performing the assays of the invention that include materials for specifically determining the expression of at least one gene within an individual cell, e.g., for specifically determining the differential expression of two or more genes within an individual cell.

The diagnostic assays described herein will also remove what is at the present time a large obstacle to successful treatment of lung cancer with extant therapeutic measures: the condition generally is not diagnosed sufficiently early. The switch from expression of COX4-2 to COX4-1 in lung cancer means that the expression/nonexpression of the COX4-2 gene provides a specific biomarker for the transition to lung cancer, and is thus an example of a sensitive, specific biomarker to diagnose lung caner.

Accordingly, certain embodiments of the present invention provide methods for detecting the presence of lung cancer in a first biological sample, including determining the level of isoform 2 of subunit 4 of cytochrome c oxidase (COX4-2) in the first biological sample, wherein a lower level of COX4-2 in the first biological sample as compared to the level of COX4-2 in a second biological sample that does not include lung cancer indicates the presence of lung cancer in the first biological sample.

Certain embodiments of the present invention provide methods for screening a subject at an elevated risk for developing lung cancer, including determining the level of isoform 2 of subunit 4 of cytochrome c oxidase (COX4-2) in a biological sample from the subject, wherein a lower level of COX4-2 in the sample as compared to the level of COX4-2 in a biological sample that does not include lung cancer indicates the that the subject has lung cancer.

Certain embodiments of the present invention provide methods for identifying and treating lung cancer in a subject, including determining the level of isoform 2 of subunit 4 of cytochrome c oxidase (COX4-2) in a biological sample from the subject, wherein a lower level of COX4-2 in the sample as compared to the level of COX4-2 in a biological sample that does not include lung cancer indicates the that the subject has lung cancer, and administering a treatment for lung cancer to the patient.

Certain embodiments of the present invention provide methods for determining whether a subject has lung cancer, including determining the level of isoform 2 of subunit 4 of cytochrome c oxidase (COX4-2) in a biological sample from the subject, wherein a lower level of COX4-2 in the sample as compared to the level of COX4-2 in a biological sample that does not include lung cancer indicates the that the subject has developed lung cancer.

In certain embodiments of the present invention, the first biological sample is obtained from a subject who is at an elevated risk for developing lung cancer. In certain embodiments of the present invention, the subject is at an elevated risk for developing lung cancer. In certain embodiments of the present invention, the subject has a history of smoking at least one form of a tobacco product. In certain embodiments of the present invention, the subject has a history of exposure to second-hand smoke. In certain embodiments of the present invention, the subject has a genetic predisposition for developing lung cancer. In certain embodiments of the present invention, the subject has a history of exposure to asbestos fibers. In certain embodiments of the present invention, the subject has a history of exposure to elevated levels of radon.

In certain embodiments of the present invention, the biological samples include sputum. In certain embodiments of the present invention, the biological samples include saliva. In certain embodiments of the present invention, the biological samples are obtained using bronchoalveolar lavage. In certain embodiments of the present invention, the biological samples include a biopsy sample of lung tissue.

In certain embodiments of the present invention, the level of COX4-2 and/or COX4-1 is determined by measuring the amount of COX4-2 mRNA and/or COX4-1 mRNA. In certain embodiments of the present invention, the level of COX4-2 and/or COX4-1 is determined by measuring the amount of COX4-2 and/or COX4-1 protein.

In certain embodiments of the present invention, the level of COX4-2 and/or COX4-1 is measured in a single cell.

In certain embodiments of the present invention, the treatment includes surgery, chemotherapy, radiation therapy, a targeted therapy, immunotherapy, or a combination thereof. In certain embodiments of the present invention, the targeted therapy includes the use of gefitinib, erlotinib, or a combination thereof.

In certain embodiments of the present invention, the method further includes administering at least one additional diagnostic test to the subject to diagnose lung cancer in the subject. In certain embodiments of the present invention, the at least one additional diagnostic test is a blood count test, a blood chemistry test, a chest x-ray, a computed tomography (CT) scan, a magnetic resonance imaging (MRI) scan, a positron emission tomography (PET) scan, sputum cytology, a needle biopsy, bronchoscopy, mediastinoscopy, mediastinotomy, thoracentesis, thoracoscopy, a bone marrow biopsy, or a combination thereof.

In certain embodiments of the present invention, the method further includes determining the level of isoform 1 of subunit 4 of cytochrome c oxidase (COX4-1) in a sample and comparing the level of COX4-2 to COX4-1, wherein a lower ration of COX4-1 to COX4-2 indicates the presence of lung cancer in the sample.

Cytochrome c Oxidase (COX)

Cytochrome c oxidase (COX) is the terminal enzyme of the mitochondrial respiratory chain and consumes the vast majority of cellular oxygen. COX is composed of 13 subunits per monomer and functions as a dimer. In addition to the 3 largest mitochondrial encoded subunits, the mammalian enzyme contains 10 nuclear encoded subunits, which are partly expressed in a tissue specific and developmental manner (Grossman et al., 1997). The role of COX as the rate-limiting enzyme of oxidative metabolism has been shown in a variety of human cell types and a mouse cell line with a mutation in COX subunit I (Villani et al., 1998; Acin-Perez et al., 2003).

COX subunit 4 (COX 4) is the largest nuclear encoded subunit and contacts catalytic subunits I and II (Tsukihara et al., 1996). For the cow heart enzyme, the ubiquitously expressed COX subunit isoform 4-1 has been shown to bind ATP on the matrix side, leading to allosteric inhibition of enzyme activity at high intramitochondrial ATP/ADP ratios (Arnold et al., 1999). This switch-like function of COX IV allows enzyme activity to be adjusted to physiological energy demand.

A lung-specific isoform of COX subunit IV (COX4-2) was recently discovered in mammals (Hüttemann et al., 2001). Northern analysis and quantitative PCR with human and rat tissues showed high COX4-2 expression in adult lung and trachea and lower expression in all other tissues investigated, including fetal lung. While not intended to be a limitation of the invention, the downregulation of the COX4-2 gene in lung cancer appears to be an important, possibly essential, step during neoplastic transformation, providing COX with the ubiquitously expressed COX4-1 isoform, which is present in low oxygen tissues; cancer cells, especially in solid tumors, are often oxygen depleted, a condition that together with the expression of the lung isoform might further impair energy production and thus cancer cell survival.

The switching from aerobic to glycolytic metabolism in tumor and transformed cells has been known for decades (Vaupel et al., 1989; Rodriguez-Enriquez and Moreno-Sanchez, 1998). Therefore, a low oxidative metabolism likely represents the physiological status of rapidly proliferating cells similar to embryonic cells (Pedersen, 1978). Indeed, lymphocytes, enterocytes, and fetal tissues are not very oxidative (Cuezva et al., 1997; Sodhi et al, 2001), whereas highly oxidative tissues such as kidney cortex or brain are normally quiescent. Strong evidence is presented herein that COX switches back to the embryonic enzyme version during lung cancer development and in cancerous cells. COX lacking the lung isoform 4-2 appears to be less active, which can be interpreted as an adaptation to a switching from aerobic to glycolytic metabolism. COX subunit 4-2 is a focal point in regulating aerobic versus anaerobic metabolism in the lung and is a functional biomarker.

Thus, in addition to being an excellent lung cancer marker, COX is also a target for therapeutic intervention. Thus, also provided herein are assays and screens useful for identifying agents that increase or decrease the expression of COX, e.g., COX4-1 and/or COX4-2. Agents that increase the expression from, e.g., the COX4-2 gene, will be useful in treating and/or preventing cancer, e.g., lung cancer.

Probe ligation and rolling circle amplification. A novel diagnostic assay is described herein. The assay combines the capabilities of both ligation-based assays and rolling circle amplification (RCA). In ligation-based assays, two recognition sequences anneal to the fragment of interest and then are ligated. When ligated, they are very stable, resisting washing steps that remove non-ligated sequences. Such ligation-based assays are extremely specific, since two independent sequences must bind simultaneously to the correct fragment (Landegren 1993; Landegren et al. 1996). In RCA, a strand displacing polymerase such as Phi 29 replicates a circular template over and over again as it proceeds along the circle under isothermal conditions. As a result, the replicated sequence is multiplied, e.g., 1,000-fold or more. Combining RCA with recognition sequences for fluorophores (e.g., molecular beacons), results in an easily visualized, highly amplified signal. The combination of ligation with RCA is attractive. However, the laboratories that work with RCA have reported difficulties. For example, difficulties have been reported amplifying padlock probes that remain catenated to their target (Christian et al. 2001). It has also been reported that so long as the probe remains catenated to the target sequence, replication of the probe does not occur (Baner et al. 1998).

Approaches to overcome steric hindrance include shortening or digesting the target sequences completely by exonucleases before amplification. However, in that case, the RCA products would no longer be tethered to the target, as is required for an in situ assay. Certain embodiments of the present invention combine the use of oligonucleotide stems that are attached to target recognition sequences and that also anneal to preformed circles with ligation-based hybridization. It is a technique that preserves the proven advantages of the specificity of ligation-based assays and the amplification power of RCA while spatially separating them so that they can each work effectively.

The Lungs and Lung Cancer

The lungs are two sponge-like organs. Air goes into the lungs through the trachea. The trachea divides into tubes called the bronchi, which divide into smaller branches called the bronchioles. At the end of the bronchioles are tiny air sacs known as alveoli. Many tiny blood vessels run through the alveoli, absorbing oxygen from the inhaled air into the bloodstream and releasing carbon dioxide. Taking in oxygen and getting rid of carbon dioxide are the lungs' main function. A slippery lining, called the pleura, surrounds the lungs. This lining protects the lungs and helps them slide back and forth as they expand and contract during breathing.

Most lung cancers start in the lining of the bronchi. That is why another term for lung cancer is bronchogenic cancer. Lung cancer can also form in glands below the lining of the bronchi, frequently in the periphery of the lungs. Lung cancers are thought to develop over a period of many years. First, there may be areas of precancerous changes in the lung. These precancerous changes often progress to true cancer. It would be very useful to be able to detect these precancerous changes. As a cancer develops, the cancer cells may produce chemicals that cause new blood vessels to form nearby. These new blood vessels nourish the cancer cells, which can continue to grow and form a tumor large enough to see on x-rays. Cells from the cancer can break away from the original tumor and spread to other parts of the body. This process is called metastasis.

There are two major types of lung cancer: small cell lung cancer (SCLC) and non-small cell lung cancer (NSCLC). If a lung cancer has characteristics of both types it is called a mixed small cell/large cell carcinoma.

About 13% of all lung cancers are the small cell type (SCLC), named for the small round cells that make up these cancers. SCLC tends to spread widely through the body. The cancer cells can multiply quickly, form large tumors, and spread to lymph nodes and other organs such as the bones, brain, adrenal glands, and liver. This type of cancer often starts in the bronchi near the center of the chest. Small cell lung cancer is almost always caused by smoking. It is very rare for someone who has never smoked to have small cell lung cancer. Other names for SCLC are oat cell carcinoma and small cell undifferentiated carcinoma.

The remaining 87% of lung cancers are non-small cell (NSCLC). There are three sub-types of NSCLC. The cells in these sub-types differ in size, shape, and chemical make-up. About 25%-30% of all lung cancers are squamous cell carcinomas. They are associated with a history of smoking and tend to be found centrally, near a bronchus. Adenocarcinomas account for about 40% of lung cancers. Adenocarcinoma is usually found in the outer region of lung. People with one type of adenocarcinoma, known as bronchioloalveolar carcinoma (sometimes called bronchoalveolar carcinoma or bronchioalveolar carcinoma) tend to have a better prognosis than those with other types of lung cancer. Large-cell undifferentiated carcinomas are a type of cancer that accounts for about 10%-15% of lung cancers. It may appear in any part of the lung, and it tends to grow and spread quickly resulting in a poor prognosis.

In addition to the 2 main types of lung cancer, other tumors can occur in the lungs. Some of these are non-cancerous (benign). Carcinoid tumors of the lung account for fewer than 5% of lung tumors. Most are slow-growing tumors that are called typical carcinoid tumors. They are generally cured by surgery. Although some typical carcinoid tumors can spread, they usually have a better prognosis than small cell or non-small cell lung cancer. Cancers intermediate between the benign carcinoids and small cell lung cancer are known as atypical carcinoid tumors.

Lung Cancer Stages

Staging is the process of determining how localized or widespread cancer is. It describes how far the cancer has spread. The treatment and prognosis depend, to a large extent, on the cancer's stage. Tests such as CT, MRI, scans, bone marrow biopsy, mediastinoscopy, and blood tests are used to stage the cancer.

Staging of Non-Small Cell Lung Cancer.

The system used to describe the growth and spread of non-small cell lung cancer (NSCLC) is the TNM staging system, also known as the American Joint Committee on Cancer (AJCC) system. T stands for tumor (its size and how far it has spread within the lung and to nearby organs), N stands for spread to lymph nodes, and M is for metastasis (spread to distant organs). In TNM staging, information about the tumor, lymph nodes, and metastasis is combined and a stage is assigned to specific TNM groupings. The grouped stages are described using the number 0 and Roman numerals from I to IV (1 to 4). Some stages are subdivided into A and B.

In some cancers, another measure called grade is used. This reflects the pathologist's assessment of how fast the cancer is growing and how likely it is to spread. This is not usually done for lung cancer.

Non-Small Cell Lung Cancer T Stages

Tis: Cancer is found only in the layer of cells lining the air passages. It has not invaded other lung tissues. This stage is also known as carcinoma in situ.

T1: The cancer is no larger than 3 centimeters (slightly less than 1¼ inches), has not spread to the membranes that surround the lungs (visceral pleura), and does not affect the main branches of the bronchi.

T2: The cancer has one or more of the following features: it is larger than 3 cm; it involves a main bronchus, but is not closer than 2 cm (about ¾ inch) to the point where the trachea (windpipe) branches into the left and night main bronchi (carina); it has spread to the membranes that surround the lungs (pleura). The cancer may partially clog the airways, but this has not caused the entire lung to collapse or develop pneumonia T3: The cancer has one or more of the following features: spread to the chest wall, the breathing muscle that separates the chest from the abdomen (diaphragm), the membranes surrounding the space between the two lungs (mediastinal pleura), or membranes of the sac surrounding the heart (parietal pericardium); invades a main bronchus and is closer than 2 cm (about ¾ inch) to the point where the windpipe (trachea) branches into the left and right main bronchi, but does not affect this area; has grown into the airways enough to cause an entire lung to collapse or to cause pneumonia in the entire lung.

T4: The cancer has one or more of the following features: spread to the space behind the chest bone and in front of the heart (mediastinum) the heart, the where the windpipe branches into the left and right main bronchi; two or more separate tumor nodules are present in the same lobe, windpipe (trachea), the esophagus (tube connecting the throat to the stomach), the backbone, or the point; there is a fluid containing cancer cells in the space surrounding the lung.

Non-Small Cell Lung Cancer N Stages

N0: No spread to lymph nodes.

N1: Spread to lymph nodes within the lung and/or located around the area where the bronchus enters the lung (hilar lymph nodes). Metastases affect lymph nodes only on the same side as the cancerous lung.

N2: Spread to lymph nodes around the point where the windpipe branches into the left and right bronchi or in the space behind the chest bone and in front of the heart (mediastinum). Affected lymph nodes are on the same side of the cancerous lung.

N3: Spread to lymph nodes near the collarbone on either side, to hilar or mediastinal lymph nodes on the side opposite the cancerous lung.

Non-Small Cell Lung Cancer M Stages

M0: No spread to distant organs or areas. Sites considered distant include other lobes of the lungs, lymph nodes further than those mentioned in N stages, and other organs or tissues such as the liver, bones, or brain M1: The cancer has spread distantly.

Stage Grouping for Non-Small Cell Lung Cancer

Once the T, N, and M categories have been assigned, this information is combined (stage grouping) to assign an overall stage of 0, I, II, III, or IV. Patients with lower stage numbers have a better prognosis.

Stage 0; Tis, N0, M0: The cancer is found only in the layer of cells lining the air passages. It has not invaded other lung tissues nor spread to lymph nodes or distant sites.

Stage IA; T1, N0, M0: The cancer is no larger than 3 centimeters, has not spread to the membranes that surround the lungs, does not affect the main branches of the bronchi and has not spread to lymph nodes or distant sites.

Stage IB; T2, N0, M0: The cancer is larger than 3 cm, or involves a main bronchus, but is not near the carina or it has spread to the pleura or the cancer is partially clogging the airways. It has not spread to lymph nodes or distant sites.

Stage IIA; T1, N1, M0: The cancer is no larger than 3 centimeters, has not spread to the membranes that surround the lungs, does not affect the main branches of the bronchi. It has spread to nearby or hilar lymph nodes, but not to distant sites.

Stage IIB; T2, N1, M0 or T3, N0, M0: The cancer is larger than 3 cm, or involves a main bronchus, but is not near the carina or it has spread to the pleura or the cancer is partially clogging the airways. It has spread to nearby or hilar lymph nodes, but not to distant sites, OR, It has spread to the chest wall or the diaphragm, the mediastinal pleura, or membranes surrounding the heart, or it invades a main bronchus and is close to the carina or it has grown into the airways enough to cause an entire lung to collapse or to cause pneumonia in the entire lung. It has not spread to lymph nodes or distant sites.

Stage IIIA; T1 or 2, N2, M0 or T3, N1 or 2, M0: The cancer can be any size, or involves a main bronchus, but is not near the carina or it has spread to the pleura or the cancer is partially clogging the airways. It has spread to nodes in the middle of the chest (mediastinum), but not to distant sites, OR, It has spread to the chest wall or the diaphragm, the mediastinal pleura, or membranes surrounding the heart, or it invades a main bronchus and is close to the carina or it has grown into the airways enough to cause an entire lung to collapse or to cause pneumonia in the entire lung. It has spread to lymph nodes anywhere in the chest on the same side as the cancer, but not to distant sites.

Stage IIIB; T1, 2 or 3, N3, M0 or T4, N0, 1, 2 or 3, M0: The cancer can be of any size. It has spread to lymph nodes around the collarbone on either side, or to hilar or mediastinal lymph nodes on the side opposite the cancerous lung OR, It has spread to the mediastinum, the heart, the windpipe (trachea), the esophagus (tube connecting the throat to the stomach), the backbone, or the carina or two or more separate tumor nodules are present in the same lobe, or there is a fluid containing cancer cells in the space surrounding the lung. The cancer may or may not have spread to lymph nodes. It has not spread to distant sites.

Stage IV; Any T, Any N, M1: The cancer has spread to distant sites.

Staging of Small Cell Lung Cancer

Although small cell lung cancers can be staged like NSCLC, most doctors prefer a 2-stage system. These are "limited stage" and "extensive stage." Limited stage usually means that the cancer is only in one lung and in lymph nodes on the same side of the chest.

Spread of the cancer to the other lung, to lymph nodes on the other side of the chest, or to distant organs indicates extensive disease. Many doctors consider small cell lung cancer that has spread to the fluid around the lung an extensive stage.

Small cell lung cancer is staged in this way because it helps separate patients who have a fair prognosis and may be cured, from those who have a worse outlook with no chance of cure. About two-thirds of the people with small cell lung cancer have extensive disease when their cancer is first found.

Thus, certain embodiments of the present invention are directed to methods for detecting lung cancer at the earliest stage possible, e.g., at or before any of the stages of presentation of lung cancer, such as those listed herein.

Certain embodiments of the invention will now be illustrated by the following non-limiting Example(s).

EXAMPLE 1

COX4-2 is Highly Expressed in Lung and Trachea

Figure 2:
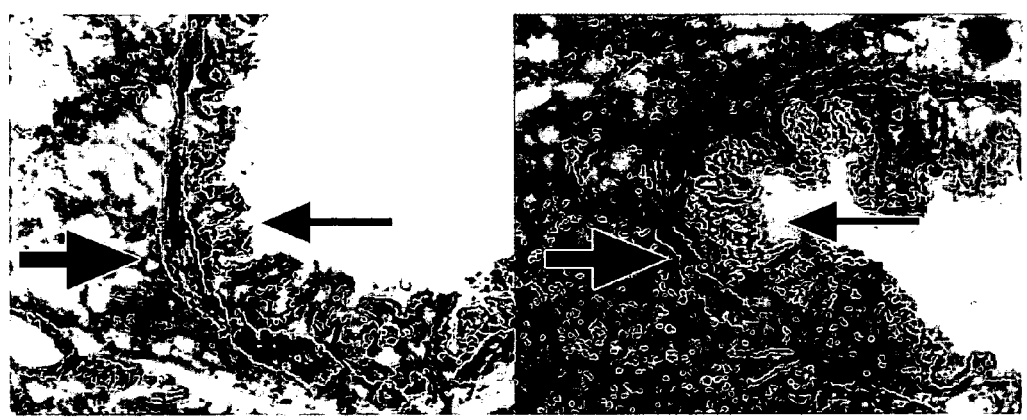
FIG. 2. In situ hybridization of cytochrome c oxidase subunit isoforms 4-1 (right) and 4-2 (left) in rat lung tissue.

The COX4-2 isoform is highly expressed in lung and trachea, where it constitutes about half the subunit 4 transcript, as determined by quantitative PCR (FIG. 1). To localize the site where COX4-2 is synthesized, in situ hybridization was performed with lung samples. These showed that message was found in smooth muscle, in addition to other lung cell types such as epithelia and fibroblasts (FIG. 2). By contrast, COX4-1 staining was strongest in the lining respiratory epithelium.

FIG. 1 depicts the relative quantitative PCR of cytochrome c oxidase subunit isoforms 4-1 and 4-2. Experiments were performed as described (Hüttemann et al., 2001). %[COX4-1]+%[COX4-2]=100%. Relative amounts of COX4-2 transcripts are indicated.

FIG. 2 depicts in situ hybridization of cytochrome c oxidase subunit isoforms 4-1 (right) and 4-2 (left) in rat lung tissue. Shown is a large bronchiole with surrounding tissue. Strong staining was detected for the 4-1 isoform in the respiratory epithelium (smaller arrow, right), whereas a stronger signal was observed for COX4-2 in smooth muscle (larger arrow, left). A control incubated with the labelled sense RNAs of both isoforms showed no staining (not shown). In situ hybridizations were carried out with a DIG-labelled antisense RNA followed by an alkaline phosphatase reaction utilizing BM-purple dye (Roche).

EXAMPLE 2

COX4-2 is Downregulated in Lung Cancer

A quantitative TaqMan real time PCR was used to investigate the changes in gene expression levels of both isoforms in six lung cancers. Fluorescent probes and primers for both COX subunit 4 isoforms were used. RNA isolation and TaqMan PCR were performed.

The quantitative PCR approach is based on the comparison of both isoform transcript levels in lung cancer and normal lung tissue. COX4-1, the ubiquitously expressed homologue to the lung gene COX4-2, can serve as an internal standard. COX4-1 shows no significant changes in cancer compared to control tissue, as shown by in situ hybridization. COX4-1 can serve as a standard with respect to COX4-2, both 1) externally, because its expression levels are similar under a variety of conditions, and 2) internally, because it is part of the same enzyme, providing a solid basis for expression changes of COX4-2.

Figure 3:
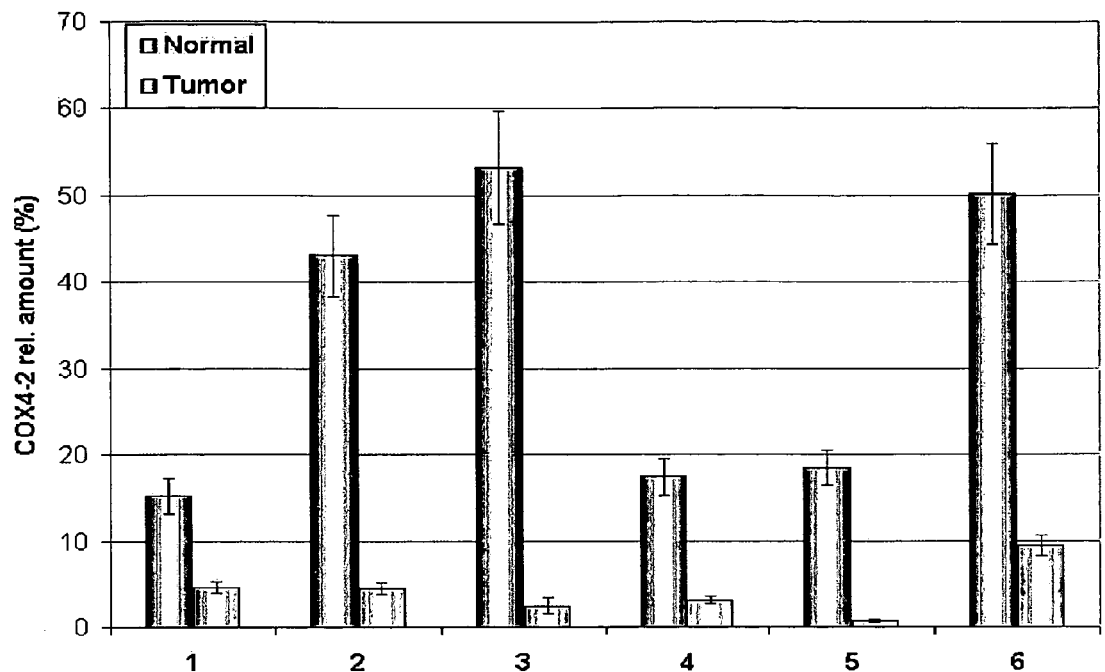
FIG. 3. Quantitative TaqMan PCR shows significant decrease of COX4-2 transcripts in the cancers of all 6 patients.
Figure 4:
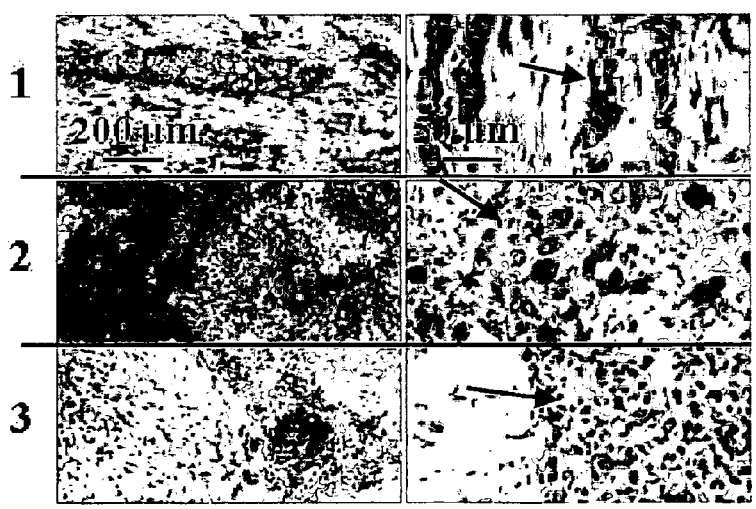
FIG. 4. Hematoxylin-Eosin (HE) stained sections. (1). A lung adenocarcinoma, showing malignant glands (arrow), surrounded by stroma, (2). A squamous cell carcinoma, composed of sheets of large polygonal cells with eosinophilic cytoplasm (arrow). (3). A mesothelioma.

Data obtained are striking in that they show a highly significant decrease in COX4-2 expression in all cancer samples including three adenocarcinomas, two squamous cell carcinomas, and a mesothelioma sample (FIG. 3). These changes were observed even though the cancer samples contained in part normal cells (see FIG. 4). The "normal" samples as defined by routine pathology of patients 1, 4, and 5 contain COX4-2 levels significantly lower compared to "normal" patient samples 2, 3, and 6. According to the hypothesis that downregulation of COX4-2 is an early process during carcinogenesis, the "normal" tissue analyzed likely contains neoplastic lesions that are undetectable using routine pathology but are easily detectable with the COX4-2/COX4-1 marker system. An analysis of stage I lung cancers revealed that COX4-2 transcription is dramatically downregulated (Table 1).

TABLE 1

COX4-2 transcript levels in four stage I lung cancer samples.

| Stage 1 lung cancers | % COX4-2 |
|---|---|
| Squamous cell carcinoma | 4.0 |
| Squamous cell carcinoma | 1.4 |
| Adenocarcinoma | 0.7 |
| Adenocarcinoma | 6.5 |

FIG. 3 depicts quantitative TaqMan PCR results and shows a significant decrease of COX4-2 transcripts in the cancers of all 6 patients. Matching normal lung tissue (blue) and lung cancer tissue (red) of six patients were analyzed. COX4-2 transcript levels were normalized to COX4-1 levels. Adenocarcinomas, patient 1, 5, and 6; squamous cell carcinomas, patients 2 and 4; mesothelioma, patient 5.

EXAMPLE 3

COX4-2 is Downregulated at Early Lung Cancer Stages

RNA samples from SV-40 immortalized but non-transforming bronchial epithelial Beas2-B cells were examined. These cells were treated with 5 µg/mL Cigarette Smoke Condensate (CSC) in DMSO to induce malignant transformation as determined by colony forming efficiency analyzed after each passage (Siddiq et al, 2004). Significant changes were observed only after passage 18 in the presence of CSC, with a more than 4 fold increase in colony forming efficiency (Siddiq et al., 2004). COX4-2 transcript levels were tested via TaqMan PCR at passage 18, but also at the earliest passage available, passage 9. Four clones were also included that were expanded from soft agar after passage 18 and CSC treatment because malignant transformation efficiency is further increased 2-3 fold (Siddiq et al., 2004). In addition, other established lung cancer cell lines were also included. Again, the data were striking in that COX4-2 transcript levels were near background level in all samples, a more than 10,000 fold downregulation, including, notably, the early passages that macroscopically are non-transforming (Table 2). Thus, COX4-2 transcription is decreased in the cancer cells, and the decrease occurs at very early stages during transformation.

TABLE 2

COX4-2 transcript levels in cell lines treated with or withhout Cigarette Smoke Condensate (CSC). Normal lung epithelial cell line Beas2-B was grown for different time periods (passage 9 and 18) and treated with CSC in DMSO and DMSO alone as control. Other cell lines when included for comparison (HTB182, 5800, 5810, 5298, H460).

| Cell line | % COX4-2 |
|---|---|
| Beas2B DMSO P9 | not detectable |
| Beas2B CSC P9 | <0.002 |
| Beas2B P9 | <0.004 |
| Beas2B P18 | not detectable |
| Beas2B DMSO P18 | not detectable |
| Beas2B CSC P18 | not detectable |
| HTB 182 | <0.002 |
| 5800 | <0.003 |
| 5810 | <0.004 |
| 5298 | <0.001 |
| H460 | not detectable |
| Beas2B Clone 1 | not detectable |
| Beas2B Clone 2 | <0.003 |
| Beas2B Clone 3 | <0.009 |
| Beas2B Clone 4 | <0.003 |

EXAMPLE 4

COX4-2 is an Early Lung Cancer Biomarker

The differential expression of the two isoforms of COX4 affords an ideal biomarker to be used in an assay for early detection of lung cancer because it involves an isoform specific to lung tissue that is downregulated in lung cancer at an early stage, and the standard against which its downregulation is measured is highly but constantly expressed and is itself the alternate isoform of the same subunit. However, the use of the COX4 early marker system and the diagnostic assay development do not depend on each other. In the case that COX4-2 is down-regulated in less than the vast majority of lung cancer samples, the proposed assay can still be used with other marker gene(s).

(a) COX4-2/COX4-1 Transcript Levels in Lung Cancers.

That COX4-2 is a lung cancer marker will be verified on a larger number of lung cancer samples and from matching controls. TaqMan real time PCR will be used with primers and fluorescent probes ("MGB"-probes, Applied Biosystems) for COX4-2 and COX4-1. RNA will be obtained from tumor samples immediately frozen after surgery and controls (ca. 150-300 mg each sample). Control lung tissue samples will be obtained from the marginal regions of the tissue. All samples that will be used will be derived from waste tissue after lung surgery. In addition, lung samples from individuals with no lung disease, in particular no lung cancer history, may be used as additional controls. Sample may include, e.g., stage 1 lung cancer samples and matching controls. COX4-2 downregulation may be found in all cancer samples.

Statistical method: Quantitative RT-PCR data will be analyzed using the Wilcoxon rank sum test, also known as the Mann-Whitney U test.

b) A Diagnostic Test for the Early Detection of Lung Cancer

It is expected that neoplastic cells will be outnumbered by normal cells and thus standard assays such as quantitative PCR or ELISA based on cell mixtures may not be optimal for early detection; the earlier the neoplastic lesion, presumably the more diluted are the malignant cells among normal cells. Thus, an assay based on individual cells is proposed herein. In certain embodiments, cells that only produce signals for the COX4-1 isoform will indicate the presence of neoplasia.

Figures 5A, 5B, 5C:
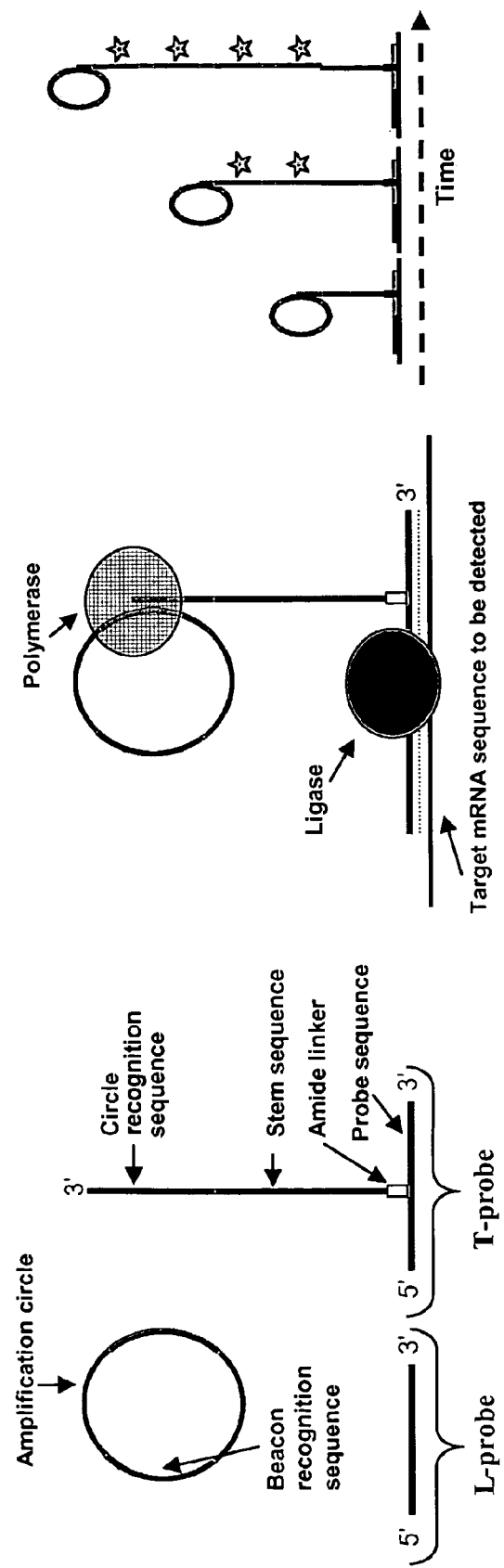
FIGS. 5A-C. A schematic representation of an assay of the invention.

Experimental design: An assay based on the differential expression of the two isoforms, a reliable in situ technique that can distinguish between cells expressing normal amounts of COX4-2, and those cells expressing markedly lower amounts or no COX4-2, is described herein. The technique is a modification of rolling circle amplification (RCA). One circular probe can be used for each of the two genes whose expression is to be detected (COX4-1 and COX4-2 in this case), with molecular beacon recognition sequences that will distinguish the two visually (amplification circle, FIG. 5A).

An advantage of using a stem-based RCA approach is to circumvent steric hindrance of the polymerase during amplification that is usually observed in standard RCA. However, specificity can be lost if only one gene-specific probe is used. In addition, robustness of the assay may sometimes problematic because washing conditions, such as salt concentration and temperature, may have to be precisely controlled: if washing occurs under too stringent conditions the stem probe can be pulled off the target mRNA, leading to false negative results.

In order to combine robust stem-based amplification with specificity, two probes for each COX4 mRNA (L- and T-probe, FIG. 5A) have been designed. Both probes anneal to adjacent regions on the target mRNA to allow subsequent amplification after they have been ligated, e.g., using T4 DNA ligase. Washing conditions can be chosen in a broad temperature window due to an about 15° C. increase of the calculated melting temperatures of the ligated probes containing the L- and T-sequence, compared to the unligated T-probes. Thus, a washing step will remove any unligated probe, which provides complete specificity, and for the signal to be generated by RCA the two recognition sequences, each unique to the gene of interest, would both have to anneal.

FIG. 5 depicts a schematic representation of an assay of the invention. As depicted in 5A, the assay involves the use an amplification circle, a T-shaped probe (T-probe), and a second probe (L-probe) to be ligated to the T-probe. As depicted in 5B, after cells have been fixed on slides, the probes are added and anneal to their target mRNA. A ligase concatenates both probes, which leads to an increased Tm for the ligated probe. Applying stringency washes, T- or L-probes that are not ligated are removed whereas the ligated probe remains bound. The single stranded amplification circle is added, which anneals to the circle recognition sequence of the T-probe, which serves as a primer for RCA. As depicted in 5C, the strand replacement polymerase extends the circle recognition sequence going around the circle many times (RCA), generating many copies of the Beacon recognition sequence for subsequent fluorescent detection (green star). This approach spatially separates the RCA reaction from the target sequence, eliminating steric hindrance of standard RCA, but still maintaining high specificity due to the requirement of the L- and T-probe ligation. The reaction can be multiplexed using different circle recognition sequences and amplification circles for the respective biomarker(s).

The probes (see Table 3) contain several features: (1) they span exon-exon junctions, preventing amplification of genomic DNA; (2) their sequences are unique with respect to the human genome and EST database; (3) the probes have similar melting temperatures, allowing washing steps under similar stringency when multiplexed; (4) the T-probe is 5'-phosphorylated to allow ligation to the L-probe; (5) the T-probes contain either a 3-carbon spacer or a di-deoxy cytosine at the 3'-end to prevent 3'-amplification of the probe, important because unspecific annealing of the T-probe to any other mRNA template could otherwise lead to the 3'-extension of the probe during the amplification phase, which would increase the melting temperature of the T-probe with its unspecific target, preventing controlled removal of misannealed probes during subsequent washing steps; and (6) the T-probe contains an amino group attached by a 6-carbon linker to a thymine nucleotide in the middle of the probe, which allows efficient synthesis of the full T-probe containing the stem part via specific coupling chemistry (see below). The position of the modified thymine nucleotide within the sequence was designed to provide enough space for the footprint of the relatively small T4 ligase on the 5'-phosphate side of the ligation to link the L- and T-probes (Ng et al., 2004, found that T4 ligase requires 6 bp on the 5'-phosphate side of the nick for efficient ligation).

TABLE 3

Specific probes for COX4-1/COX4-2 detection. The T-probes contain a 5'-phosphate (P), and C$_6$-amino modified T base (*), and a 3'-spacer (spC3) or a dideoxy 3' base (ddC).

| | L-probe | T-probe |
|---|---|---|
| COX4-1 | 5'-TACGAGCTCATGAAAGTGT TGTGAAGAGC-3' (SEQ ID NO:1) | 5'-P-GAAGACTTTT*CGCTC CCAGspC3-3' (SEQ ID NO:2) |
| COX4-2 | 5'-TTGGTGGCAGCGGGTCTAC GTATTTCCTC-3' (SEQ ID NO:3) | 5'-P-CAAAGCCGAT*CACCT TGAddC-3' (SEQ ID NO:4) |

Table 3. Specific probes for COX4-1/COX4-2 detection. The T-probes contain a 5'-phosphate (P), and C$_6$-amino modified T base (*), and a 3'-spacer (spC3) or a dideoxy 3' base (ddC).

Coupling reaction: To generate the T-probe, which includes the sequence complementary to the target mRNA and the stem for initiating RCA, diimide coupling chemistry will be utilized, which specifically links a carboxyl with an amine moiety, generating an amide bond: in the presence of the water-soluble compound EDC (1-ethyl-3-[3-dimethylaminopropyl]carbodiimide hydrochloride) the amide bond is specifically formed, preventing the formation of by-products as observed when using mono-functional coupling reactions (see Reaction 1). The coupling reaction products will be analyzed by mass spectrometry.

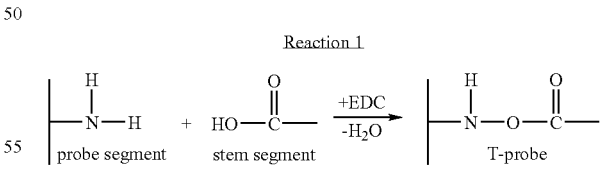

Reaction 1

Assay performance. Cells will be fixed on a slide. During this process membrane holes are generated, allowing enzymes, probes, and other components to enter the cells. L- and T-probes of both COX4 isoforms are annealed to their target RNAs and only ligated if annealed immediately adjacent on the same mRNA strand. Unligated probes will be removed by a washing step at elevated temperature followed by the addition of amplification circles, which anneal to the stem part of T-probe. Extension of the circles will be performed using Phi 29 polymerase for 1 hr at 30° C., and terminated by a washing step. Beacon probes specific for either isoform amplification product will be annealed. A washing step will remove unincorporated beacon probes and the cells will be visualized with a two channel fluorescent microscope.

The assay may be modified by the art worker, starting from the following conditions:

(1) Fixation of cells. The cells will be suspended in SSC. 200 μL will be placed on slides cleaned with ethanol. The slides will then be placed in a cytocentrifuge (700 rpm for 4 min). The slides with fixed cells will be then bathed in methanol to perforate the cells while leaving them and their contents in place. The methanol will be evaporated to dry the cells.

(2) Annealing and ligation of the probes. Annealing and ligation will be performed in ligation buffer (30 mM Tris-HCl (pH 7.8), 1 mM $MgCl_2$, 10 mM DTT and 1 mM ATP) containing 1 μM T-probe, 1 μL-probe, 3 μM preformed circles, and 20 units T4 DNA ligase (Promega). Appropriate control mixtures will also be made, in which circles, ligase, T-probes, and L-probes are in turn missing from the mixture. The solution will be applied to the slides and held in place by a gasket and cover (MJ Research). The mixture will be ligated for two hours at room temperature.

(3) Washing. The gaskets and covers will be removed, and the slides will be washed in 2×SSC buffer at 65° C. for 5 min with agitation in order to remove unligated T-probe and unannealed circles. The slides will be then air dried.

(4) RCA. DNA syntheses will be performed in amplification buffer (4 mM Tris-HCl (pH 7.5), 5 mM KCl, 1 mM $MgCl_2$, 0.5 mM $(NH_4)_2SO_4$, 0.4 mM DTT, and 1 μM dNTPs) in the presence of 20 units Phi 29 polymerase (Epicentre). Twenty-five μL of this solution will be applied to each slide, and a gasket and cover will be applied. Slides will be incubated at 30° C. for 1 hour, washed in 2×SSC for 5 min at room temperature, and then soaked in PBS (pH 8), supplemented with 0.1% Nonidet for 5 min at room temperature, in order to remove the polymerase.

(5) Molecular beacons. The circles will be of two types, each including a recognition sequence for one of two different molecular beacons, one that will incorporate the fluorescent dye Oregon Green and will indicate the presence of COX4-2, and another that will incorporate the fluorescent dye Texas Red and will indicate the presence of COX4-1. These fluorescent dyes show clearly distinguishable emission spectra (542 nm and 615 nm, respectively). The beacon recognition sequences have been designed such that the recognition sequence includes the quencher stem sequence, so that the quencher, when annealed, will be held next to the amplified RCA DNA strand, while the fluorophore's hairpin/stem will be free from the amplified product. This will prevent one beacon's quencher from quenching a neighboring beacon's fluorophore (Nilsson et al., 2002). The beacons (4 μM) along with annealing buffer (30 mM Tris-HCl (pH 7.8), 10 mM $MgCl_2$, 10 mM DTT) will be added to the RCA reaction products on the slides, and the mixture will be heated to 70° C. to denature the beacons, and then cooled to room temperature to allow them to anneal to the recognition sequences. The slides will then be soaked in SSC at room temperature for 5 min, and then soaked in PBS (pH 8), with 0.1% Nonidet for 5 min at room temperature, to remove unbound beacons to further reduce background signal.

(6) Data analysis. The slides will be visualized using a Nikon E-600 FE fluorescent microscope connected to a Retiga 1300 digital camera and will be analyzed with Simple PCI image capture software (Compix).

Different salt concentrations may be used in the ligation step. The ligation and RCA steps may be combined in order to make the assay simpler. In doing so, the buffer composition may be modified to be compatible with both T4 ligase and Phi 29 polymerase. The amount of molecular beacon used in step (5) will be optimized for maximum signal with minimum background.

Phase I: Two established human H460 derived cell lines, one overexpressing COX4-1 and the other overexpressing COX4-2 will be examined. These cell lines have been generated by cloning the two COX4 isoform cDNAs in the pcDNA-his/myc vector (Invitrogen), which contains the neo cassette. Transfected cells were selected using G418 and clones containing the genomic plasmid insertion were expanded for four weeks in media containing G418. A mouse fibroblast cell line will be used as negative controls (CRL-2017, available from ATCC). The assay will be optimized for each isoform separately. A successful assay will be able to specifically distinguish cells expressing one isoform from cells expressing the other. The next step is the combination (multiplexing) of both assays. The assay will also be tested on human tissue sections derived from normal and lung cancer samples. Although the primary goal is to develop a non-invasive lung cancer test based on sputum, saliva, and BAL samples, the in situ assay is expected to work similarly well on tissue sections obtained from surgery or biopsies, which will be an additional useful application for the detection of early stages of neoplastic transformation in tissues obtained by more invasive means.

Phase II: Material from lung cancer patients with different types and stages of cancer will be examined. Specimens to be used in these investigations include biological samples such as sputum and BAL samples from individuals screened as high risk for developing lung cancer, including chronic smokers with evidence of chronic obstructive pulmonary disease. Some bronchial biopsies from these patients as well as from patients with established lung cancer will be used. Sputum analysis may be part of these programs, followed by bronchoscopy in positive cases, which are available in addition to control samples. These samples will be matched for clinical pathological parameters, including smoking history, age, and gender. Sputum and snap-frozen tissue specimens will be promptly delivered to the laboratory. Cells will be collected by centrifugation and divided onto three slides (50-70 cells/slide). The first slide will be used for routine cytological evaluation, the second slide will be used for ligation-based RCA, and the third will be stored frozen at −80° C. for follow up studies or the repetition of the assay in ambiguous cases. Tissue samples will be used to (1) generate at least five 12 micron serial frozen tissue sections for H-E and the assay, and (2) 10-40 mg of the remaining tissue will be used for TaqMan PCR.

Data interpretation, sample size, and alternative outcome. Sputum samples from smokers and ex-smokers will be analyzed. The sputum samples may be stored as cell pellets in cryomedia. Analysis will begin on the subset of samples form individuals with known lung cancer and controls. It is expected that the cancer patient-derived samples will show a higher number of cells not expressing COX4-2. Cells that do not show signals for the control (COX4-1) will not be considered. In the population of cells producing signals for COX4-1 the ratio of cells will be determined that show a lower, e.g., absent, signal for COX4-2. The more advanced the cancer lesion, the more abundant will be cells lacking COX4-2 transcripts. The in situ assay regarding COX4-2 in individual cells will produce easily distinguishable data such that the transcripts are present (normal cells) or absent (all cancer stages). However, in case gradually variable COX4-2 levels are observed after normalization to COX4-1 levels, e.g., in the very earliest stages of transformation, the data analysis will be modified accordingly: instead of having the expected two categories, COX4-2 being absent or present, the scale will be expanded to five categories. The assignment of the categories to cancer advancement will be based on results derived from individuals with known lung cancer and control samples.

Statistical method: Data will be analysed with the Wilcoxon rank sum test (in case binary data are obtained, in which cancer cells express no COX4-2) or t-test (if continuous data are obtained, in which case cancer cells would show a gradual decrease in COX4-2 expression as cancer progresses).

The capacity of the assay for multiplexing means that several biomarkers could be identified in one reaction. The assay can be applied to a variety of other biological samples, such as blood, cell smears, and tissue sections.

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

All publications, patents and patent applications listed herein are herein incorporated by reference.

DOCUMENTS

American Cancer Society (2002) Cancer facts and figures. 2002.
Acin-Perez et al.: (2003) An intragenic suppressor in the cytochrome c oxidase I gene of mouse mitochondrial DNA. Hum Mol Genet 12 329-39.
Archer et al.: (2002) The mechanism(s) of hypoxic pulmonary vasoconstriction: potassium channels, redox O(2) sensors, and controversies. News Physiol Sci 17 131-7.
Arnold et al.: (1999) The intramitochondrial ATP/ADP-ratio controls cytochrome c oxidase activity allosterically. FEBS Lett 443 105-8.
Avanzo et al.: (2004) Increased susceptibility to urethane-induced lung tumors in mice with decreased expression of Connexin 43. Carcinogenesis.
Barros et al: (2001) Hypoxic metabolic response of the golden-mantled ground squirrel. J Appl Physiol 91 603-12.
Baty et al.: (2002) Detection of oxidant sensitive thiol proteins by fluorescence labeling and two-dimensional electrophoresis. Proteomics 2 1261-6.
Boehle et al.: (2002) Wortmannin inhibits growth of human non-small-cell lung cancer in vitro and in vivo. Langenbecks Arch Surg 387 234-9.
Burke et al.: (1998) Structure/function of oxygen-regulated isoforms in cytochrome c oxidase. J Exp Biol 201 (Pt 8) 1163-75.
Cantley: (2002) The phosphoinositide 3-kinase pathway. Science 296 1655-7.
Chandel et al.: (2000) Cellular oxygen sensing by mitochondria: old questions, new insight. J Appl Physiol 88 1880-9.
Cuezva et al.: (1997) Mitochondrial biogenesis in the liver during development and oncogenesis. J Bioenerg Biomembr 29 365-77.
Epstein et al.: (1978) A theoretical analysis of the barometric method for measurement of tidal volume. Respir Physiol 32 105-20.
Esamai: (1998) Relationship between exposure to tobacco smoke and bronchial asthma in children: a review. East Afr Med J 75 47-50.
Ferguson-Miller et al.: (1976) Correlation of the kinetics of electron transfer activity of various eukaryotic cytochromes c with binding to mitochondrial cytochrome c oxidase. J Biol Chem 251 1104-15.
Gnaiger et al.: (1998) Mitochondrial oxygen affinity, respiratory flux control and excess capacity of cytochrome c oxidase. J Exp Biol 201 (Pt 8) 1129-39.
Green et al.: (2003) Management of asthma in adults: current therapy and future directions. Postgrad Med J 79 259-67.
Grossman et al.: (1997) Nuclear genes for cytochrome c oxidase. Biochim Biophys Acta 1352 174-92.
Gyuris et al.: (1993) Cdi1, a human G1 and S phase protein phosphatase that associates with Cdk2. Cell 75 791-803.
Hirsch et al.: (1997) Prevention and early detection of lung cancer-clinical aspects. Lung Cancer 17 163-74.
Hüttemann et al.: (2003a) Cytochrome c oxidase of mammals contains a testes-specific isoform of subunit VIb—the counterpart to testes-specific cytochrome c? Mol Reprod Dev 66 8-16.
Hüttemann et al.: (2001) Mammalian subunit IV isoforms of cytochrome c oxidase. Gene 267 111-23.
Hüttemann et al.: (2003b) A third isoform of cytochrome c oxidase subunit VIII is present in mammals. Gene 312 95-102.
Jacky: (1980) Barometric measurement of tidal volume: effects of pattern and nasal temperature. J Appl Physiol 49 319-25.
Joad et al.: (2004) Passive smoke effects on cough and airways in young guinea pigs: role of brainstem substance P. Am J Respir Crit Care Med 169 499-504.
Kadenbach et al.: (2004) The possible role of cytochrome c oxidase in stress-induced apoptosis and degenerative diseases. Biochim Biophys Acta 1655 400-8.
Kolonin et al.: (2000) Interaction mating methods in two-hybrid systems. Methods Enzymol 328 26-46.
Korshunov et al.: (1997) High protonic potential actuates a mechanism of production of reactive oxygen species in mitochondria. FEBS Lett 416 15-8.
Kosower et al.: (1995) Diamide: an oxidant probe for thiols. Methods Enzymol 251 123-33.
Li et al.: (2002) Lung pathology in platelet-derived growth factor transgenic mice: effects of genetic background and fibrogenic agents. Exp Lung Res 28 507-22.
Lin et al.: (2001) Overexpression of phosphatidylinositol 3-kinase in human lung cancer. Langenbecks Arch Surg 386 293-301.
Lundblad et al.: (2002) A reevaluation of the validity of unrestrained plethysmography in mice. J Appl Physiol 93 1198-207.
Malkinson: (1989) The genetic basis of susceptibility to lung tumors in mice. Toxicology 54 241-71.
Miller et al.: (2003) Induction of a high incidence of lung tumors in C57BL/6 mice with multiple ethyl carbamate injections. Cancer Lett 198 139-44.
Napiwotzki et al.: (1997) ATP and ADP bind to cytochrome c oxidase and regulate its activity. Biol Chem 378 1013-21.
Ng et al.: (2004) Protein-DNA footprinting by endcapped duplex oligodeoxyribonucleotides. Nucleic Acids Res 32 e107.
Nilsson et al.: (2002) Real-time monitoring of rolling-circle amplification using a modified molecular beacon design. Nucleic Acids Res 30 e66.
Pedersen: (1978) Tumor mitochondria and the bioenergetics of cancer cells. Prog Exp Tumor Res 22 190-274.
Robinson-White et al.: (2002) Protein kinase A signaling: "cross-talk" with other pathways in endocrine cells. Ann N Y Acad Sci 968 256-70.

Rodriguez-Enriquez et al.: (1998) Intermediary metabolism of fast-growth tumor cells. Arch Med Res 29 1-12.

Ryan et al.: (1987) KRAS2 as a genetic marker for lung tumor susceptibility in inbred mice. J Natl Cancer Inst 79 1351-7.

Santillan et al.: (2003) A meta-analysis of asthma and risk of lung cancer (United States). Cancer Causes Control 14 327-34.

Schuller et al.: (2004) Neuroendocrine lung carcinogenesis in hamsters is inhibited by green tea or theophylline while the development of adenocarcinomas is promoted: implications for chemoprevention in smokers. Lung Cancer 45 11-8.

SEER: Cancer facts and statistics. SEER, 1998.

Siddiq et al.: (2004) Increased osteonectin expression is associated with malignant transformation and tumor associated fibrosis in the lung. Lung Cancer 45 197-205.

Sodhi et al.: (2001) Hypoxia and high glucose cause exaggerated mesangial cell growth and collagen synthesis: role of osteopontin. Am J Physiol Renal Physiol 280 F667-74.

Suh et al.: (1999) Cell transformation by the superoxide-generating oxidase Mox1. Nature 401 79-82.

Tsukihara et al.: (1996) The whole structure of the 13-subunit oxidized cytochrome c oxidase at 2.8 A. Science 272 1136-44.

Vaupel et al.: (1989) Blood flow, oxygen and nutrient supply, and metabolic microenvironment of human tumors: a review. Cancer Res 49 6449-65.

Villani et al.: (1998) Low reserve of cytochrome c oxidase capacity in vivo in the respiratory chain of a variety of human cell types. J Biol Chem 273 31829-36.

von Wangenheim et al.: (1998) Control of cell proliferation by progress in differentiation: clues to mechanisms of aging, cancer causation and therapy. J Theor Biol 193 663-78.

Wong-Riley: (1979) Changes in the visual system of monocularly sutured or enucleated cats demonstrable with cytochrome oxidase histochemistry. Brain Res 171 11-28.

Yamamoto et al: (1977) Fluorometric studies on the light chains of skeletal muscle myosin. I. Effects of temperature, ionic strength, divalent metal ions, and nucleotides. J Biochem (Tokyo) 82 747-52.

You et al.: (1992) Parental bias of Ki-ras oncogenes detected in lung tumors from mouse hybrids. Proc Natl Acad Sci USA 89 5804-8.

Zhong et al.: (2003) A strategy for constructing large protein interaction maps using the yeast two-hybrid system: regulated expression arrays and two-phase mating. Genome Res 13 2691-9.

---

The invention claimed is:

1. A method for detecting the presence of lung cancer in a first biological sample, comprising determining the level of RNA for isoform 2 of subunit 4 of cytochrome c oxidase (COX4-2) in the first biological sample, wherein a lower level of COX4-2 RNA in the first biological sample as compared to the level of COX4-2 RNA in a second biological sample that does not comprise lung cancer indicates the presence of lung cancer in the first biological sample, wherein the first and second biological sample comprises lung cells.

2. A method for screening a subject at risk for developing lung cancer, comprising determining the level of RNA for isoform 2 of subunit 4 of cytochrome c oxidase (COX4-2) in a biological sample from the subject, wherein a lower level of COX4-2 RNA in the sample as compared to the level of COX4-2 RNA in a biological sample that does not comprise lung cancer indicates that the subject has lung cancer, wherein the biological sample comprises lung cells.

3. A method for identifying and treating lung cancer in a subject, comprising determining the level of RNA for isoform 2 of subunit 4 of cytochrome c oxidase (COX4-2) in a biological sample from the subject, wherein a lower level of COX4-2 RNA in the sample as compared to the level of COX4-2 RNA in a biological sample that does not comprise lung cancer indicates that the subject has lung cancer, and administering a treatment for lung cancer to the subject, wherein the biological sample comprises lung cells.

4. A method for determining whether a subject has lung cancer, comprising determining the level of RNA for isoform 2 of subunit 4 of cytochrome c oxidase (COX4-2) in a biological sample from the subject, wherein a lower level of COX4-2 RNA in the sample as compared to the level of COX4-2 RNA in a biological sample that does not comprise lung cancer indicates that the subject has developed lung cancer, wherein the biological sample comprises lung cells.

5. The method of claim 1, wherein the first biological sample is obtained from a subject who is at risk for developing lung cancer.

6. The method of claim 3, wherein the subject is at risk for developing lung cancer.

7. The method of claim 2, wherein the subject has a history of smoking at least one form of a tobacco product.

8. The method of claim 2, wherein the subject has a history of exposure to second-hand smoke.

9. The method of claim 2, wherein the subject has a genetic predisposition for developing lung cancer.

10. The method of claim 2, wherein the subject has a history of exposure to asbestos fibers.

11. The method of claim 2, wherein the subject has a history of exposure to radon.

12. The method of claim 1, wherein the biological samples comprise sputum.

13. The method of claim 1, wherein the biological samples are obtained using bronchoalveolar lavage.

14. The method of claim 1, wherein the biological samples comprise a biopsy sample of lung tissue.

15. The method of claim 1, wherein the level of COX4-2 is determined by measuring the amount of COX4-2 mRNA.

16. The method of claim 1, wherein the level of COX4-2 RNA is measured in a single cell.

17. The method of claim 3, wherein the treatment comprises surgery, chemotherapy, radiation therapy, a targeted therapy, immunotherapy, or a combination thereof.

18. The method of claim 17, wherein the targeted therapy comprises the use of gefitinib, erlotinib, or a combination thereof.

19. The method of claim 2, further comprising administering at least one additional diagnostic test to the subject to diagnose lung cancer in the subject.

20. The method of claim 19, wherein the at least one additional diagnostic test is a blood count test, a blood chemistry test, a chest x-ray, a computed tomography (CT) scan, a magnetic resonance imaging (MRI) scan, a positron emission tomography (PET) scan, sputum cytology, a needle biopsy, bronchoscopy, mediastinoscopy, mediastinotomy, thoracentesis, thoracoscopy, a bone marrow biopsy, or a combination thereof.

21. The method of claim 1, further comprising determining the level of RNA for isoform 1 of subunit 4 of cytochrome c oxidase (COX4-1) in a sample and comparing the level of COX4-2 RNA to COX4-1 RNA, wherein a lower level of COX4-1 RNA than COX4-2 RNA indicates the presence of lung cancer in the sample.

* * * * *